US012734236B2

(12) United States Patent
Lugovskoy et al.

(10) Patent No.: US 12,734,236 B2
(45) **Date of Patent: *Sep. 15, 2026**

(54) ANTI-VLA-4 ANTIBODIES

(71) Applicant: BIOGEN MA INC., Cambridge, MA (US)

(72) Inventors: Alexey A. Lugovskoy, Woburn, WA (US); Frederick R. Taylor, Milton, MA (US); Karen McLachlan, Solana Beach, CA (US)

(73) Assignee: BIOGEN MA INC., Cambridge, MA (US)

( * ) Notice: Subject to any disclaimer, the term of this patent is extended or adjusted under 35 U.S.C. 154(b) by 763 days.

This patent is subject to a terminal disclaimer.

(21) Appl. No.: 18/165,146

(22) Filed: Feb. 6, 2023

(65) Prior Publication Data

US 2024/0100155 A1 Mar. 28, 2024

Related U.S. Application Data

(60) Division of application No. 17/366,903, filed on Jul. 2, 2021, now Pat. No. 11,571,477, which is a division of application No. 16/441,974, filed on Jun. 14, 2019, now Pat. No. 11,083,791, which is a continuation of application No. 15/838,884, filed on Dec. 12, 2017, now Pat. No. 10,335,485, which is a continuation of application No. 13/641,199, filed as application No. PCT/US2011/032641 on Apr. 15, 2011, now abandoned.

(60) Provisional application No. 61/324,944, filed on Apr. 16, 2010.

(51) Int. Cl.
*A61K 39/395* (2006.01)
*A61K 45/06* (2006.01)
*C07K 16/28* (2006.01)
*C07K 16/30* (2006.01)

(52) U.S. Cl.
CPC ........ *A61K 39/39558* (2013.01); *A61K 45/06* (2013.01); *C07K 16/2839* (2013.01); *C07K 16/2842* (2013.01); *C07K 16/3061* (2013.01); *C07K 2317/24* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS 4,399,216 A 8/1983 Axel et al.
4,439,196 A 3/1984 Higuchi
4,447,224 A 5/1984 Decant, Jr. et al.
4,447,233 A 5/1984 Mayfield
4,475,196 A 10/1984 La Zor
4,486,194 A 12/1984 Ferrara
4,487,603 A 12/1984 Harris
4,494,880 A 1/1985 Su
4,596,556 A 6/1986 Morrow et al.
4,634,665 A 1/1987 Axel et al.
4,790,824 A 12/1988 Morrow et al.
4,816,397 A 3/1989 Boss et al.
4,816,567 A 3/1989 Cabilly et al.
4,816,587 A 3/1989 Megyeri et al.
4,833,092 A 5/1989 Geysen
4,941,880 A 7/1990 Burns
5,064,413 A 11/1991 Mckinnon et al.
5,179,017 A 1/1993 Axel et al.
5,217,870 A 6/1993 Hession et al.
5,260,210 A 11/1993 Rubin et al.
5,272,263 A 12/1993 Hession et al.
5,312,335 A 5/1994 Mckinnon et al.
5,367,056 A 11/1994 Hession et al.
5,383,851 A 1/1995 Mckinnon, Jr. et al.
5,399,163 A 3/1995 Peterson et al.
5,530,101 A 6/1996 Queen et al.
5,585,089 A 12/1996 Queen et al.
5,648,260 A 7/1997 Winter et al.
5,672,622 A 9/1997 Hedgepeth et al.
5,693,761 A 12/1997 Queen et al.
5,693,762 A 12/1997 Queen et al.
5,695,755 A 12/1997 Papayannopoulou
5,789,650 A 8/1998 Lonberg et al.
5,798,230 A 8/1998 Bornkamm et al.
5,824,304 A 10/1998 Papayannopoulou
5,840,299 A 11/1998 Bendig et al.
5,843,438 A 12/1998 Papayannopoulou
5,849,992 A 12/1998 Meade et al.
5,859,205 A 1/1999 Adair et al.
5,871,734 A 2/1999 Lobb et al.
5,888,507 A 3/1999 Burkly (Continued)

FOREIGN PATENT DOCUMENTS

EP 239400 A2 9/1987
EP 2050462 A1 4/2009

(Continued)

OTHER PUBLICATIONS

Quann et al. Natalizumab for GVHD: too little or too late? Blood Advances, 7(17):5187-5187, 2023 (Year: 2023).*

(Continued)

*Primary Examiner* — Maher M Haddad

(74) *Attorney, Agent, or Firm* — McCarter & English, LLP; Jill Mello

(57) ABSTRACT

This invention relates to alpha-4 binding antibodies, and fragments thereof.

14 Claims, 9 Drawing Sheets

Specification includes a Sequence Listing.

(56) References Cited

U.S. PATENT DOCUMENTS 5,932,214 A 8/1999 Lobb et al.
6,033,665 A 3/2000 Yednock
6,153,653 A 11/2000 Shashoua
6,252,043 B1 6/2001 Hession et al.
6,277,393 B1 8/2001 Yrjanheikki et al.
6,307,025 B1 10/2001 Hession et al.
6,407,213 B1 6/2002 Carter et al.
6,432,404 B1 8/2002 Gallatin et al.
6,482,409 B1 11/2002 Lobb et al.
6,509,376 B1 1/2003 Joshi et al.
6,602,503 B1 8/2003 Lobb et al.
6,616,926 B1 9/2003 Burkly et al.
6,680,302 B2 1/2004 Seidman et al.
6,894,033 B2 5/2005 Cruz et al.
7,094,397 B2 8/2006 Stratton et al.
7,157,086 B2 1/2007 Lobb et al.
7,232,830 B2 6/2007 Delack
7,482,003 B2 1/2009 Lobb et al.
7,557,190 B2 7/2009 Barbosa et al.
7,576,101 B2 8/2009 Karlik et al.
7,678,371 B2 3/2010 Lugovskoy et al.
7,829,092 B2 11/2010 Lobb et al.
10,335,485 B2 * 7/2019 Lugovskoy ............ A61K 45/06
11,083,791 B2 * 8/2021 Lugovskoy ........ C07K 16/2839
11,571,477 B2 * 2/2023 Lugovskoy ............. A61P 35/00
12,037,398 B2 * 7/2024 Ferrant-Orgettas .......................... C07K 16/2842
2002/0025348 A1 2/2002 Basu et al.
2003/0070185 A1 4/2003 Jakobovits et al.
2003/0135887 A1 7/2003 Brandle et al.
2003/0223972 A1 12/2003 Goldman et al.
2003/0232333 A1 12/2003 Ladner et al.
2004/0009163 A1 1/2004 Schimmel et al.
2004/0009169 A1 1/2004 Taylor et al.
2004/0043931 A1 3/2004 Hersberg et al.
2004/0110226 A1 6/2004 Lazar et al.
2004/0203031 A1 10/2004 Whitehead et al.
2005/0053598 A1 3/2005 Burke et al.
2005/0074443 A1 4/2005 Treadwell
2005/0215565 A1 9/2005 Karlik et al.
2006/0235207 A1 10/2006 Tsuchiya et al.
2006/0258852 A1 11/2006 Lugovskoy et al.
2007/0004775 A1 1/2007 Perry
2007/0048255 A1 3/2007 Hunter
2008/0025971 A1 1/2008 Fong et al.
2008/0075719 A1 3/2008 Chan et al.
2009/0004189 A1 1/2009 Behrens et al.
2009/0169477 A1 7/2009 Panzara et al.
2009/0202527 A1 8/2009 Panzara et al.
2011/0318346 A1 12/2011 Steinman et al.
2014/0161794 A1 6/2014 Lugovskoy et al.
2021/0238289 A1 8/2021 Ferrant-Orgettas et al.

FOREIGN PATENT DOCUMENTS

JP 8-507680 A 8/1996
JP 9-508272 A 8/1997
JP 2000-500501 A 1/2000
JP 2007-531761 A 11/2007
JP 2008-531060 A 8/2008
WO WO-1986/01533 A1 3/1986
WO WO-1986/05807 A1 10/1986
WO WO-1987/04462 A1 7/1987
WO WO-1989/01036 A1 2/1989
WO WO-1989/07454 A1 8/1989
WO WO-1989/10404 A1 11/1989
WO WO-1990/07861 A1 7/1990
WO WO-1990/13300 A1 11/1990
WO WO-1991/09967 A1 7/1991
WO WO-1992/000995 A1 1/1992
WO WO-1992/04381 A1 3/1992
WO WO-1993/13798 A1 7/1993
WO WO-1993/15764 A1 8/1993
WO WO-1994/11027 A1 5/1994
WO WO-1994/16094 A2 7/1994
WO WO-1994/17818 A1 8/1994
WO WO-1995/019790 A1 7/1995
WO WO-1996/07861 A1 3/1996
WO WO-1996/34096 A1 10/1996
WO WO-1997/018838 A1 5/1997
WO WO-1998/004247 A1 2/1998
WO WO-1999/06436 A1 2/1999
WO WO-1999/61421 A1 12/1999
WO WO-2001/55112 A1 8/2001
WO WO-2002/30488 A2 4/2002
WO WO-2003/072040 A2 9/2003
WO WO-2005/047327 A2 5/2005
WO WO-2005/099776 A2 10/2005
WO WO-2006/023629 A2 3/2006
WO WO-2006/23649 A2 3/2006
WO WO-2006/055871 A2 5/2006
WO WO-2006/060787 A2 6/2006
WO WO-2006/096653 A2 9/2006
WO WO-2006/131200 A1 12/2006
WO WO-2007/140249 A1 12/2007
WO WO-2008/021954 A2 2/2008
WO WO-2008/143954 A2 11/2008
WO WO-2008/157356 A2 12/2008
WO WO-2010/085682 A2 7/2010
WO WO-2011/130603 A2 10/2011
WO WO-2013/057092 A1 4/2013
WO WO-2014/150973 A1 9/2014

OTHER PUBLICATIONS

Hanf et al. Antibody humanization by redesign of complementarity-determining region residues proximate to the acceptor framework. Methods 65 (2014) 68-76. (Year: 2014).*

U.S. Appl. No. 13/641,199, filed Nov. 25, 2013, 2014-0161794, Abandoned.

U.S. Appl. No. 15/838,884, filed Dec. 12, 2017, U.S. Pat. No. 11,335,485, Issued U.S. Appl. No. 16/441,974, filed Jun. 14, 2019, U.S. Pat. No. 11,083,791, Issued.

U.S. Appl. No. 17/366,903, filed Jul. 2, 2021, U.S. Pat. No. 11,571,477, Issued.

U.S. Appl. No. 15/734,915, filed Dec. 3, 2020, 2021-0238289, Pending.

Ansel et al., Pharmaceutical Dosage Forms and Drug Delivery Systems, Seventh Edition. Lippincott Williams & Wilikins, (1999).

Apatoff, Multiple Sclerosis (MS). Merck Manual, retrieved online at: http://www.merckmanuals.com/home/print/brain_spinal_cord_and_nerve_disorders. 5 pages, (2008).

Arai, The usefulness of oligoclonal bands in cerebrospinal fluids for diagnosis in multiple sclerosis. Jpn J Electroph. 2000;44(4):295-300.

Arnason, Interferon beta in multiple sclerosis. Neurology. Apr. 1993;43(4):641-3.

Attwood, Genomics. The Babel of bioinformatics. Science. Oct. 20, 2000;290(5491):471-3.

Ausubel et al., Hybridization with Radioactive Probes. Current Protocols in Molecular Biology. pp. 6.3.1-6.3.6, (1993).

Barcellos et al., Chromosome 19 single-locus and multilocus haplotype associations with multiple sclerosis. Evidence of a new susceptibility locus in Caucasian and Chinese patients. JAMA. Oct. 15, 1997;278(15):1256-61.

Barkof et al., Comparison of MRI criteria at first presentation to predict conversion to clinically definite multiple sclerosis. Brain. Nov. 1997;120 ( Pt 11):2059-69.

Bavbek et al., Monoclonal antibodies against ICAM-1 and CD18 attenuate cerebral vasospasm after experimental subarachnoid hemorrhage in rabbits. Stroke. Sep. 1998;29(9):1930-5.

Beck et al., The effect of corticosteroids for acute optic neuritis on the subsequent development of multiple sclerosis. The Optic Neuritis Study Group. N Engl J Med. Dec. 9, 1993;329(24):1764-9.

Becker et al., Antibody to the alpha4 integrin decreases infarct size in transient focal cerebral ischemia in rats. Stroke. Jan. 2001;32(1):206-11.

(56) References Cited

OTHER PUBLICATIONS

Becker et al., Immunologic tolerance to myelin basic protein decreases stroke size after transient focal cerebral ischemia. Proc Natl Acad Sci U S A. Sep. 30, 1997;94(20):10873-8.
Beers et al., Inflammatory Bowel Disease. The Merck Manual of Diagnosis and Therapy, Seventeenth Edition. Merck Research Laboratories, Whitehouse Station, NJ. Chapter 31, pp. 302-312, (1999).
Berge et al., Pharmaceutical salts. J Pharm Sci. Jan. 1977;66(1):1-19.
Berger et al., Progressive multifocal leukoencephalopathy: lessons from AIDS and natalizumab. Neurol Res. Apr. 2006;28(3):299-305.
Bilinska et al., Progression of multiple sclerosis is associated with exon 1 CTLA-4 gene polymorphism. Acta Neurol Scand. Jul. 2004;110(1):67-71.
Bird et al., Single-chain antigen-binding proteins. Science. Oct. 21, 1988;242(4877):423-6.
Boerner et al., Production of antigen-specific human monoclonal antibodies from in vitro-primed human splenocytes. J Immunol. Jul. 1, 1991;147(1):86-95.
Bot et al., Differentiation of multiple sclerosis from other inflammatory disorders and cerebrovascular disease: value of spinal MR imaging. Radiology. Apr. 2002;223(1):46-56.
Brex et al., Assessing the risk of early multiple sclerosis in patients with clinically isolated syndromes: the role of a follow up Mri. J Neurol Neurosurg Psychiatry. Mar. 2001;70(3):390-3.
Burton et al., Human antibody effector function. Adv Immunol. 1992;51:1-84.
Business Wire, Antegren one-year data from phase III Affirm study showed compelling results in metting primary endpoint in multiple sclerosis. https://www.thefreelibrary.com/_/print/PrintArticle.aspx?id=124245420, 3 pages, Nov. 8, 2004.
Calabresi et al., VLA-4 expression on peripheral blood lymphocytes is downregulated after treatment of multiple sclerosis with interferon beta. Neurology. Oct. 1997;49(4):1111-6.
Campanero et al., An alternative leukocyte homotypic adhesion mechanism, LFA-1/ICAM-1-independent, triggered through the human VLA-4 integrin. J Cell Biol. Jun. 1990;110(6):2157-65.
Cancer.gov, Genetic Tools for Modeling Leukemia and Lymphoma in the Mouse. National Cancer Institute, retrieved online at: https://web.archive.org/web/20041031161411/http://emice.nci.nih.gov/emice/mouse_models/organ_models/hema_models/hema_mouse_tools/selected_references. 2 pages, Oct. 31, 2004.
Chen et al., Enhancement and destruction of antibody function by somatic mutation: unequal occurrence is controlled by V gene combinatorial associations. EMBO J. Jun. 15, 1995;14(12):2784-94.
Chothia et al., Canonical structures for the hypervariable regions of immunoglobulins. J Mol Biol. Aug. 20, 1987;196(4):901-17.
Choudry et al., Single patient study for the emergency use of natalizumab (Antegren) in the treatment of pediatric multiple sclerosis. Neurology. 2004;62(Suppl 5):A488-A489, Abstract P06.082.
Clark et al., Antibodies against Mac-1 attenuate neutrophil accumulation after traumatic brain injury in rats. J Neurotrauma. Jun. 1996;13(6):333-41.
Clark et al., Reduction of central nervous system ischemic injury in rabbits using leukocyte adhesion antibody treatment. Stroke. Jul. 1991;22(7):877-83.
Colman, Effects of amino acid sequence changes on antibody-antigen interactions. Res Immunol. Jan. 1994;145(1):33-6.
Csanaky et al., Adhesion receptors on peripheral blood leukemic B cells. A comparative study on B cell chronic lymphocytic leukemia and related lymphoma/leukemias. Leukemia. Mar. 1997;11(3):408-15.
Cuypers et al., Discriminative power of visual evoked potential characteristics in multiple sclerosis. Doc Ophthalmol. 1995;90(3):247-57.
Dalton et al., Early development of multiple sclerosis is associated with progressive grey matter atrophy in patients presenting with clinically isolated syndromes. Brain. May 2004;127(Pt 5):1101-7.
Dalton et al., Effect of natalizumab on conversion of gadolinium enhancing lesions to T1 hypointense lesions in relapsing multiple sclerosis. J Neurol. Apr. 2004;251(4):407-13.
Damiano et al., Cell adhesion mediated drug resistance (CAM-DR): role of integrins and resistance to apoptosis in human myeloma cell lines. Blood. Mar. 1, 1999;93(5):1658-67.
Damiano et al., Cell adhesion-mediated drug resistance (CAM-DR) protects the K562 chronic myelogenous leukemia cell line from apoptosis induced by BCR/ABL inhibition, cytotoxic drugs, and gamma-irradiation. Leukemia. Aug. 2001;15(8):1232-9.
De La Fuente et al., Engagement of alpha4beta1 integrin by fibronectin induces in vitro resistance of B chronic lymphocytic leukemia cells to fludarabine. J Leukoc Biol. Mar. 2002;71(3):495-502.
De La Fuente et al., Fibronectin interaction with alpha4beta1 integrin prevents apoptosis in B cell chronic lymphocytic leukemia: correlation with Bcl-2 and Bax. Leukemia. Feb. 1999;13(2):266-74.
De Waele et al., Different expression of adhesion molecules on CD34+ cells in AML and B-lineage ALL and their normal bone marrow counterparts. Eur J Haematol. Sep. 1999;63(3):192-201.
Devlin et al., Random peptide libraries: a source of specific protein binding molecules. Science. Jul. 27, 1990;249(4967):404-6.
Dillman, The history and rationale for monoclonal antibodies in the treatment of hematologic malignancy. Curr Pharm Biotechnol. Dec. 2001;2(4):293-300.
Doctor's Guide, Antegren one-year data show compelling results in metting primary endpoint in multiple sclerosis. Retrieved online at: http://www.pslgroup.com/dg/247956.htm. 3 pages, Nov. 9, 2004.
Drillenburg et al., Preferential expression of the mucosal homing receptor integrin alpha 4 beta 7 in gastrointestinal non-Hodgkin's lymphomas. Am J Pathol. Mar. 1997;150(3):919-27.
Edan et al., Rationale for the use of mitoxantrone in multiple sclerosis. J Neurol Sci. Aug. 15, 2004;223(1):35-9.
Elkins et al., Primary Results of the ACTION trial of Natalizumab in Acute Ischemic Stroke (AIS). International Stroke Conference. pp. 1-16, (2016).
Endo, Review/Advances in Neurological Therapeutics (2003) Multiple Sclerosis. Neurological Therapeutics. 2004;21(4):387-392.
Fazekas et al., Criteria for an increased specificity of MRI interpretation in elderly subjects with suspected multiple sclerosis. Neurology. Dec. 1988;38(12):1822-5.
Ferguson et al., Two integrin-binding peptides abrogate T cell-mediated immune responses in vivo. Proc Natl Acad Sci U S A. Sep. 15, 1991;88(18):8072-6.
Filippini et al., Interferons in relapsing remitting multiple sclerosis: a systematic review. Lancet. Feb. 15, 2003;361(9357):545-52.
Fleming et al., Alpha4beta1 integrin blockade after spinal cord injury decreases damage and improves neurological function. Exp Neurol. Dec. 2008;214(2):147-59.
Fox et al., Multiple sclerosis: the importance of early recognition and treatment. Cleve Clin J Med. Feb. 2001;68(2):157-71.
Frohman et al., The utility of MRI in suspected MS: report of the Therapeutics and Technology Assessment Subcommittee of the American Academy of Neurology. Neurology. Sep. 9, 2003;61(5):602-11.
Galetta et al., The effects of natalizumab on disability progression as measured by the Multiple Sclerosis Functionally Composite (MSFC) and visual function in patients with relapsing MS. Journal of Neurological Sciences. Jan. 1, 2005;238:S71-S72, Abstract OPI.100.
Garcia et al., Influx of leukocytes and platelets in an evolving brain infarct (Wistar rat). Am J Pathol. Jan. 1994;144(1):188-99.
Gazitt et al., Mobilization of myeloma cells involves SDF-1/CXCR4 signaling and downregulation of VLA-4. Stem Cells. 2004;22(1):65-73.
Gonzalez et al., Complex interactions between the laminin alpha 4 subunit and integrins regulate endothelial cell behavior in vitro and angiogenesis in vivo. Proc Natl Acad Sci U S A. Dec. 10, 2002;99(25):16075-80.
Grayson et al., alphadbeta2 integrin is expressed on human eosinophils and functions as an alternative ligand for vascular cell adhesion molecule 1 (VCAM-1). J Exp Med. Dec. 7, 1998;188(11):2187-91.

(56) References Cited

OTHER PUBLICATIONS

Green et al., Antigen-specific human monoclonal antibodies from mice engineered with human Ig heavy and light chain YACs. Nat Genet. May 1994;7(1):13-21.
Hall et al., Heterophilic interactions between cell adhesion molecule L1 and alphavbeta3- integrin induce HUVEC process extension in vitro and angiogenesis in vivo. Angiogenesis. 2004;7(3):213-23.
Hall et al., Regulation of lymphoid and myeloid leukemic cell survival: role of stromal cell adhesion molecules. Leuk Lymphoma. Jan. 2004;45(1):35-48.
Hamada et al., Involvement of an intercellular adhesion molecule 1-dependent pathway in the pathogenesis of secondary changes after spinal cord injury in rats. J Neurochem. Apr. 1996;66(4):1525-31.
Hart et al., Modelling of multiple sclerosis: lessons learned in a non-human primate. Lancet Neurol. Oct. 2004;3(10):588-97.
Hemler et al., Characterization of the cell surface heterodimer VLA-4 and related peptides. J Biol Chem. Aug. 25, 1987;262(24):11478-85.
Herbener et al., Functional relevance of in vivo half antibody exchange of an IgG4 therapeutic antibody-drug conjugate. PLoS One. Apr. 19, 2018;13(4):e0195823, 22 pages.
Hernan et al., Recombinant hepatitis B vaccine and the risk of multiple sclerosis: a prospective study. Neurology. Sep. 14, 2004;63(5):838-42.
Hokibara et al., Effects of monoclonal antibodies to adhesion molecules on eosinophilic myocarditis in Toxocara canis-infected CBA/J mice. Clin Exp Immunol. Nov. 1998;114(2):236-44.
Holzmann et al., alpha 4 integrins and tumor metastasis. Curr Top Microbiol Immunol. 1998;231:125-41.
Hoogenboom et al., Antibody phage display technology and its applications. Immunotechnology. Jun. 1998;4(1):1-20.
Hoogenboom et al., Natural and designer binding sites made by phage display technology. Immunol Today. Aug. 2000;21(8):371-8.
Huang et al., Construction of representative immunoglobulin variable region cDNA libraries from human peripheral blood lymphocytes without in vitro stimulation. J Immunol Methods. Aug. 9, 1991;141(2):227-36.
Huston et al., Protein engineering of antibody binding sites: recovery of specific activity in an anti-digoxin single-chain Fv analogue produced in *Escherichia coli*. Proc Natl Acad Sci U S A. Aug. 1988;85(16):5879-83.
Issekutz et al., Effect of a new monoclonal antibody, TA-2, that inhibits lymphocyte adherence to cytokine stimulated endothelium in the rat. J Immunol. Jul. 1, 1991;147(1):109-16.
Jacobs et al., Intramuscular interferon beta-1a for disease progression in relapsing multiple sclerosis. The Multiple Sclerosis Collaborative Research Group (MSCRG). Ann Neurol. Mar. 1996;39(3):285-94.
Jander et al., ascular cell adhesion molecule-1 mRNA is expressed in immune-mediated and ischemic injury of the rat nervous system. J Neuroimmunol. Oct. 1996;70(1):75-80.
Jefferis et al., IgG-Fc-mediated effector functions: molecular definition of interaction sites for effector ligands and the role of glycosylation. Immunol Rev. Jun. 1998;163:59-76.
Jiang et al., A novel peptide isolated from a phage display peptide library with trastuzumab can mimic antigen epitope of HER-2. J Biol Chem. Feb. 11, 2005;280(6):4656-62.
Jin et al., A homing mechanism for bone marrow-derived progenitor cell recruitment to the neovasculature. J Clin Invest. Mar. 2006;116(3):652-62.
Jin et al., Integrin alpha4beta1 promotes monocyte trafficking and angiogenesis in tumors. Cancer Res. Feb. 15, 2006;66(4):2146-52.
Kabat et al., Sequences of Proteins of Immunological Interest, 5th Edition, vol. 4. US Department of Human Services, NIH, (1991).
Kapadia et al., Soluble TNF binding proteins modulate the negative inotropic properties of TNF-alpha in vitro. Am J Physiol. Feb. 1995;268(2 Pt 2):H517-25.
Kaplan et al., VEGFR1-positive haematopoietic bone marrow progenitors initiate the pre- metastatic niche. Nature. Dec. 8, 2005;438(7069):820-7.
Kaufman et al., Amplification and expression of sequences cotransfected with a modular dihydrofolate reductase complementary dna gene. J Mol Biol. Aug. 25, 1982;159(4):601-21.
Kazuya et al., Current Status of Clinical Research on Immunotherapy. Clinica, 1996;23(5):389-393.
Kibbe, Handbook of Pharmaceutical Excipients. American Pharmaceutical Association, Third Edition, (2000).
Knoblach et al., Early neuronal expression of tumor necrosis factor-alpha after experimental brain injury contributes to neurological impairment. J Neuroimmunol. Mar. 1, 1999;95(1-2):115-25.
Kohlschutter et al., Drug delivery in acute myeloid leukemia. Expert Opin Drug Deliv. Jun. 2008;5(6):653-63.
Komoriya et al., The minimal essential sequence for a major cell type-specific adhesion site (CS1) within the alternatively spliced type III connecting segment domain of fibronectin is leucine-aspartic acid-valine. J Biol Chem. Aug. 15, 1991;266(23):15075-9.
Kurtze, Rating neurologic impairment in multiple sclerosis: an expanded disability status scale (EDSS). Neurology. Nov. 1983;33(11):1444-52.
Kurtzke, Clinical definition for multiple sclerosis treatment trials. Ann Neurol. 1994;36 Suppl:S73-9.
Kussie et al., A single engineered amino acid substitution changes antibody fine specificity. J Immunol. Jan. 1, 1994;152(1):146-52.
Labinez et al., Infusion of an antialpha4 integrin antibody is associated with less neoadventitial formation after balloon injury of porcine coronary arteries. Can J Cardiol. Feb. 2000;16(2):187-96.
Liesz et al., Inhibition of lymphocyte trafficking shields the brain against deleterious neuroinflammation after stroke. Brain. Mar. 2011;134(Pt 3):704-20.
Lin et al., Very late antigen 4 (VLA4) antagonists as anti-inflammatory agents. Curr Opin Chem Biol. Aug. 1998;2(4):453-7.
Lobb et al., The pathophysiologic role of alpha 4 integrins in vivo. J Clin Invest. Nov. 1994;94(5):1722-8.
Lobb et al., The role of alpha 4 integrins in lung pathophysiology. Eur Respir J Suppl. Aug. 1996;22:104s-108s.
Mabon, Strategies to Reduce Inflammation in the Central Nervous System. Submitted in partial fulfillment of the requirements for the degree of Master of Science. The University of Western Ontario, London, Ontario, Canada, Jan. 1999, 138 pages.
Masellis-Smith et al., Adhesion of multiple myeloma peripheral blood B cells to bone marrow fibroblasts: a requirement for CD44 and alpha4beta7. Cancer Res. Mar. 1, 1997;57(5):930-6.
Matsunaga et al., Combination therapy of an anticancer drug with the FNIII14 peptide of fibronectin effectively overcomes cell adhesion-mediated drug resistance of acute myelogenous leukemia. Leukemia. Feb. 2008;22(2):353-60.
Matsunaga et al., Interaction between leukemic-cell VLA-4 and stromal fibronectin is a decisive factor for minimal residual disease of acute myelogenous leukemia. Nat Med. Sep. 2003;9(9):1158-65.
Mcdonald et al., Are magnetic resonance findings predictive of clinical outcome in therapeutic trials in multiple sclerosis? The dilemma of interferon-beta. Ann Neurol. Jul. 1994;36(1):14-8.
Mcdonald et al., Recommended diagnostic criteria for multiple sclerosis: guidelines from the International Panel on the diagnosis of multiple sclerosis. Ann Neurol. Jul. 2001;50(1):121-7.
Michigami et al., Cell-cell contact between marrow stromal cells and myeloma cells via VCAM-1 and alpha(4)beta(1)-integrin enhances production of osteoclast-stimulating activity. Blood. Sep. 1, 2000;96(5):1953-60.
Miller et al., A controlled trial of natalizumab for relapsing multiple sclerosis. N Engl J Med. Jan. 2, 2003;348(1):15-23.
Miller et al., Gadolineum enhances (Gd+) lesions and baseline relapse rate as potential predictors of disease activity and responsiveness to natalizemab (Antegren) treatment in subjects with relapsing multiple sclerosis (MS). Multiple Sclerosis. 2003;9(Suppl 1):S140- S141, Abstract P562.
Miller et al., Natalizumab (anti-VLA4 antibody) in multiple sclerosis. Colloquim C15: natalizumab (anti-VLA4 antibody) in multiple sclerosis. Journal of NeuroChemistry. Jan. 1, 2003;85(Suppl 1):96, Abstract C15-04.

(56) References Cited

OTHER PUBLICATIONS

Miller et al., Natalizumab (anti-VLA4 antibody) in multiple sclerosis. Journal of Neurochemistry. 2003;85(Suppl 1):96. Abstract C15-04.
Mohle et al., Differential expression of L-selectin, VLA-4, and LFA-1 on CD34+ progenitor cells from bone marrow and peripheral blood during G-CSF-enhanced recovery. Exp Hematol. Dec. 1995;23(14):1535-42.
Moller et al., Adhesion molecules VLA-1 to VLA-6 define discrete stages of peripheral B lymphocyte development and characterize different types of B cell neoplasia. Leukemia. Apr. 1992;6(4):256-64.
Mori et al., Anti-alpha4 integrin antibody suppresses the development of multiple myeloma and associated osteoclastic osteolysis. Blood. Oct. 1, 2004;104(7):2149-54.
Mulligan et al., Cytokine and adhesion molecule requirements for lung injury induced by anti-glomerular basement membrane antibody. Inflammation. Aug. 1998;22(4):403-17.
Nakao et al., Synergistic effect of TNF-alpha in soluble VCAM-1-induced angiogenesis through alpha 4 integrins. J Immunol. Jun. 1, 2003;170(11):5704-11.
Nowlin et al., A novel cyclic pentapeptide inhibits alpha 4 beta 1 and alpha 5 beta 1 integrin-mediated cell adhesion. J Biol Chem. Sep. 25, 1993;268(27):20352-9.
O'Connor et al., Safety, tolerability and immunogenicity of natalzumab: results from the AFFIRM trial. Neurology. Mar. 1, 2005;64(6 Suppl 1):A146, Abstract S16.004.
O'Riordan et al., The prognostic value of brain MRI in clinically isolated syndromes of the CNS. A 10-year follow-up. Brain. Mar. 1998;121 ( Pt 3):495-503.
Olerup et al., HLA class II-associated genetic susceptibility in multiple sclerosis: a critical evaluation. Tissue Antigens. Jul. 1991;38(1):1-15.
Paavonen et al., In vivo evidence of the role of alpha 4 beta 1-VCAM-1 interaction in sarcoma, but not in carcinoma extravasation. Int J Cancer. Jul. 15, 1994;58(2):298-302.
Papadopoulos et al., Pattern of expression of integrins in alveolar epithelia of fetal and adult lungs and interstitial lung diseases. Verh Dtsch Ges Pathol. 1993;77:292-5.
Patti et al., A double blind, placebo-controlled, phase II, add-on study of cyclophosphamide (CTX) for 24 months in patients affected by multiple sclerosis on a background therapy with interferon-beta study denomination: Cyclin. J Neurol Sci. Aug. 15, 2004;223(1):69-71.
Paty et al., Interferon beta-1b is effective in relapsing-remitting multiple sclerosis. II. MRI analysis results of a multicenter, randomized, double-blind, placebo-controlled trial. UBC MS/MRI Study Group and the IFNB Multiple Sclerosis Study Group. Neurology. Apr. 1993;43(4):662-7.
Paty et al., MRI in the diagnosis of MS: a prospective study with comparison of clinical evaluation, evoked potentials, oligoclonal banding, and CT. Neurology. Feb. 1988;38(2):180-5.
Pericak-Vance et al., Linkage and association analysis of chromosome 19q13 in multiple sclerosis. Neurogenetics. Oct. 2001;3(4):195-201.
Perkin et al., IgG ratios and oligoclonal IgG in multiple sclerosis and other neurological disorders. J Neurol Sci. Aug.-Sep. 1983;60(3):325-36.
Persson et al., Generation of diverse high-affinity human monoclonal antibodies by repertoire cloning. Proc Natl Acad Sci U S A. Mar. 15, 1991;88(6):2432-6.
Peters et al., Engineering an improved IgG4 molecule with reduced disulfide bond heterogeneity and increased Fab domain thermal stability. J Biol Chem. Jul. 13, 2012;287(29):24525-33.
Polman et al., A randomized, placebo-controlled trial of natalizumab for relapsing multiple sclerosis. N Engl J Med. Mar. 2, 2006;354(9):899-910.
Polman et al., Clinical results from AFFIRM: a randomized, double-blind, placebo-controlled, multicenter natalizumab in patients with relapsing multiple sclerosis. Neurology. Mar. 2005;64(6, Suppl 1):A146, Abstract S16.003.
Polman et al., New and emerging treatment options for multiple sclerosis. Lancet Neurol. Sep. 2003;2(9):563-6.
Poon et al., Emigrated neutrophils regulate ventricular contractility via alpha4 integrin. Circ Res. Jun. 11, 1999;84(11):1245-51.
Poser et al., New diagnostic criteria for multiple sclerosis: guidelines for research protocols. Ann Neurol. Mar. 1983;13(3):227-31.
Powers et al., Expression of single-chain Fv-Fc fusions in Pichia pastoris. J Immunol Methods. May 1, 2001;251(1-2):123-35.
Pozzilli et al., Corticosteroids treatment. J Neurol Sci. Aug. 15, 2004;223(1):47-51.
Press et al., Ricin A-chain containing immunotoxins directed against different epitopes on the CD2 molecule differ in their ability to kill normal and malignant T cells. J Immunol. Dec. 15, 1988;141(12):4410-7.
Pugliatti et al., Multiple sclerosis distribution in northern Sardinia: spatial cluster analysis of prevalence. Neurology. Jan. 22, 2002;58(2):277-82.
Pulido et al., Functional evidence for three distinct and independently inhibitable adhesion activities mediated by the human integrin VLA-4. Correlation with distinct alpha 4 epitopes. J Biol Chem. Jun. 5, 1991;266(16):10241-5.
Purse, Therapeutic Level, Therapeutic Drug Level—Definition. About.com, retrieved online at: http://bipolar.about.com/cd/glossaryt/g/gltherapeutic_level.htm. 4 pages, Oct. 1, 2015.
Rapalino et al., Implantation of stimulated homologous macrophages results in partial recovery of paraplegic rats. Nat Med. Jul. 1998;4(7):814-21.
Reindl et al., Antibodies against the myelin oligodendrocyte glycoprotein and the myelin basic protein in multiple sclerosis and other neurological diseases: a comparative study. Brain. Nov. 1999;122 ( Pt 11):2047-56.
Relton et al., Inhibition of alpha4 integrin protects against transient focal cerebral ischemia in normotensive and hypertensive rats. Stroke. Jan. 2001;32(1):199-205.
Remington, Remington: The Science and Practice of Pharmacy, 20th Edition. Lippincott Williams and Wilkins. 2100 pages, (2000).
Riechmann et al., Reshaping human antibodies for therapy. Nature. Mar. 24, 1988;332(6162):323-7.
Riemer et al., Matching of trastuzumab (Herceptin) epitope mimics onto the surface of Her-2/neu—a new method of epitope definition. Mol Immunol. May 2005;42(9):1121-4.
Rizzo et al., Risk of developing multiple sclerosis after uncomplicated optic neuritis: a long- term prospective study. Neurology. Feb. 1988;38(2):185-90.
Robinson et al., Controlled Drug Delivery: Fundamentals and Applications, Second Edition. CRC Press. 744 pages, (1987).
Roy-Chaudhury et al., Adhesion molecule interactions in human glomerulonephritis: importance of the tubulointerstitium. Kidney Int. Jan. 1996;49(1):127-34.
Rudick et al., Baseline patient characteristics of the SENTINEL study: a study designed to determine the efficacy and safety of natalizumab (Antegren) in combination with interferon b-1a (Avonex) for the treatment of relapsing-remitting multiple sclerosis (RRMS). Multiple Sclerosis. 2003;9(Suppl 1):S141-S142, Abstract P565.
Rudick et al., Natalizumab: alpha 4-integrin antagonist selective adhesion molecule inhibitors for MS. Expert Rev Neurother. Jul. 2004;4(4):571-80.
Rudick et al., Study designs of two phase III trials to determine the safety and efficacy of natalizumab (Antegren) alone and when added to Interferon b-1a (Aveonex) in patients with relapsing-remitting multiple sclerosis. Neurology. 2003;60(5, Suppl 1):A479. Abstract P06.102.
Rudikoff et al., Single amino acid substitution altering antigen-binding specificity. Proc Natl Acad Sci U S A. Mar. 1982;79(6):1979-83.
Sadovnick et al., The genetics of multiple sclerosis. Clin Neurol Neurosurg. Jul. 2002;104(3):199-202.

(56) References Cited

OTHER PUBLICATIONS

Sanchez-Madrid et al., VLA-3: a novel polypeptide association within the VLA molecular complex: cell distribution and biochemical characterization. Eur J Immunol. Nov. 1986;16(11):1343-9.
Sandborn et al., Efficacy assessment of natalizumab in patients with Crohn's disease and prior history of anti-TNF therapy: results from ENACT-1. Database Biosis, Biosciences Information Service, Philadelphia, PA, 1 page, (2004).
Sandborn et al., Efficacy Assessment of Natalizumab in Patients with Crohn's Disease and Prior History of Anti-TNF Therapy: Results from ENACT-1. Gastroenterology. 2004, p. A-76, Abstract 583.
Schiffer et al., A multiple sclerosis cluster associated with a small, north-central Illinois community. Arch Environ Health. Sep.-Oct. 2001;56(5):389-95.
Schmidt et al., Association of polymorphisms in the apolipoprotein E region with susceptibility to and progression of multiple sclerosis. Am J Hum Genet. Mar. 2002;70(3):708-17.
Schnell et al., Acute inflammatory responses to mechanical lesions in the CNS: differences between brain and spinal cord. Eur J Neurosci. Oct. 1999;11(10):3648-58.
Schnell et al., Cytokine-induced acute inflammation in the brain and spinal cord. J Neuropathol Exp Neurol. Mar. 1999;58(3):245-54.
Schwartz et al., Autoimmunity for Central Nervous System Maintenance, Regeneration, and Renewal: Development of a T Cell-Based Vaccination Against Neurodegeneration. Stem Cell and Gene-Based Therapy: Frontiers in Regenerative Medicine. Chapter 18, pp. 251-257, (2006).
Schwartz et al., Innate and adaptive immune responses can be beneficial for CNS repair. Trends Neurosci. Jul. 1999;22(7):295-9.
Schwartz et al., Potential repair of rat spinal cord injuries using stimulated homologous macrophages. Neurosurgery. May 1999;44(5):1041-5;.
Schwartz et al., Protection Autoimmunity in Acute and Chronic CNS Disorders. Therapeutic Vaccines, Immunolog, and Hematopoiesis. 2002:234-235.
Scott et al., Searching for peptide ligands with an epitope library. Science. Jul. 27, 1990;249(4967):386-90.
Sipe et al., A neurologic rating scale (NRS) for use in multiple sclerosis. Neurology. Oct. 1984;34(10):1368-72.
Skolnick et al., From genes to protein structure and function: novel applications of computational approaches in the genomic era. Trends Biotechnol. Jan. 2000;18(1):34-9.
Sobel et al., The immunopathology of experimental allergic encephalomyelitis. I. Quantitative analysis of inflammatory cells in situ. J Immunol. May 1984;132(5):2393-401.
Soderstrom et al., Optic neuritis: prognosis for multiple sclerosis from MRI, CSF, and HLA findings. Neurology. Mar. 1998;50(3):708-14.
Soilu-Hanninen et al., Therapy with antibody against leukocyte integrin VLA-4 (CD49d) is effective and safe in virus-facilitated experimental allergic encephalomyelitis. J Neuroimmunol. Jan. 1997;72(1):95-105.
Sotgiu et al., Treatment of refractory epilepsy with natalizumab in a patient with multiple sclerosis. Case report. BMC Neurol. Sep. 23, 2010;10:84, 8 pages.
Spelman et al., Comparative efficacy of switching to natalizumab in active multiple sclerosis. Ann Clin Transl Neurol. Apr. 2015;2(4):373-87.
Stancovski et al., Mechanistic aspects of the opposing effects of monoclonal antibodies to the ERBB2 receptor on tumor growth. Proc Natl Acad Sci U S A. Oct. 1, 1991;88(19):8691-5.
Sweet, Natalizumab update. Am J Health Syst Pharm. Apr. 1, 2007;64(7):705-16.
Tagliaferri et al., harmacological modulation of peptide growth factor receptor expression on tumor cells as a basis for cancer therapy. Anticancer Drugs. Aug. 1994;5(4):379-93.
Taylor et al., Survival signals within the tumour microenvironment suppress drug-induced apoptosis: lessons learned from B lymphomas. Endocr Relat Cancer. Mar. 1999;6(1):21-3.
Ter Brugge et al., A mouse model for chronic lymphocytic leukemia based on expression of the SV40 large T antigen. Blood. Jul. 2, 2009;114(1):119-27.
Tintore et al., Isolated demyelinating syndromes: comparison of different MR imaging criteria to predict conversion to clinically definite multiple sclerosis. AJNR Am J Neuroradiol. Apr. 2000;21(4):702-6.
Traugott et al., Detailed analysis of early immunopathologic events during lesion formation in acute experimental autoimmune encephalomyelitis. Cell Immunol. Mar. 1989;119(1):114-29.
Tubridy et al., The effect of anti-alpha4 integrin antibody on brain lesion activity in MS. The UK Antegren Study Group. Neurology. Aug. 11, 1999;53(3):466-72.
Tuohy et al., A synthetic peptide from myelin proteolipid protein induces experimental allergic encephalomyelitis. J Immunol. Aug. 15, 1988;141(4):1126-30.
Uchiyama et al., Characterization of adhesion molecules on human myeloma cell lines. Blood. Nov. 1, 1992;80(9):2306-14.
Ulrich et al., Induction of Severe Arthritis in SCID Mice by Intraarticular Injection of Cultured Rheumatoid Synovium Fibroblasts. Arthritis & Rheumatism. 1996 Sept;39(9):S284. Abstract 1539.
Urlaub et al., Isolation of Chinese hamster cell mutants deficient in dihydrofolate reductase activity. Proc Natl Acad Sci U S A. Jul. 1980;77(7):4216-20.
Vaughan et al., Human antibodies with sub-nanomolar affinities isolated from a large non-immunized phage display library. Nat Biotechnol. Mar. 1996;14(3):309-14.
Velders et al., Immunotherapy with low and high affinity monoclonal antibodies 17-1A and 323/A3 in a nude mouse xenograft carcinoma model. Cancer Res. Oct. 1, 1995;55(19):4398- 403.
Verhoeyen et al., Reshaping human antibodies: grafting an antilysozyme activity. Science. Mar. 25, 1988;239(4847):1534-6.
Vollmer et al., An open-label safety and drug interaction study of natalizumab (Antegren) in combination with interferon-beta (Avonex) in patients with multiple sclerosis. Mult Scler. Oct. 2004;10(5):511-20.
Wahl et al., Synthetic fibronectin peptides suppress arthritis in rats by interrupting leukocyte adhesion and recruitment. J Clin Invest. Aug. 1994;94(2):655-62.
Walinsky et al., Rational therapy for relapsing multiple sclerosis. Lancet Neurol. May 2003;2(5):271-2.
Ward et al., Binding activities of a repertoire of single immunoglobulin variable domains secreted from *Escherichia coli*. Nature. Oct. 12, 1989;341(6242):544-6.
Weekes et al., VLA-4 mediated adhesion to bone marrow stromal cells confers chemoresistance to adherent lymphoma cells. Leuk Lymphoma. Feb. 2001;40(5-6):631-45.
Williams et al., The immunoglobulin superfamily—domains for cell surface recognition. Annu Rev Immunol. 1988;6:381-405.
Witzig, The role of adhesion receptors in the pathogenesis of multiple myeloma. Hematol Oncol Clin North Am. Dec. 1999;13(6):1127-43.
Yanaka et al., Neuronal protection from cerebral ischemia by synthetic fibronectin peptides to leukocyte adhesion molecules. J Cereb Blood Flow Metab. Nov. 1996;16(6):1120-5.
Yednock et al., Prevention of experimental autoimmune encephalomyelitis by antibodies against alpha 4 beta 1 integrin. Nature. Mar. 5, 1992;356(6364):63-6.
Yin et al., Models of acute myeloid leukemia: Prospects for drug development and testing. Drug Discovery Today: Disease Models. 2006;3(2):137-142.
European Office Action—Response—for Application No. 11730120.0, dated Apr. 30, 2015, 8 pages.
European Office Action—Response—for Application No. 11730120.0, dated Mar. 7, 2014, 10 pages.
European Office Action for Application No. 05007878.1, dated Oct. 24, 2013, 7 pages.
European Office Action for Application No. 05804218.5, dated Dec. 15, 2008.
European Office Action for Application No. 0582495.4, dated Jun. 16, 2010, 13 pages.

(56) References Cited

OTHER PUBLICATIONS

European Office Action for Application No. 05824954.1, dated Apr. 29, 2010.
European Office Action for Application No. 05853017.1, dated Nov. 5, 2008.
European Office Action for Application No. 11730120.0, dated Aug. 28, 2013, 21 pages.
European Office Action for Application No. 11730120.0, dated Aug. 5, 2016, 11 pages.
European Office Action for Application No. 11730120.0, dated Jan. 26, 2016, 7 pages.
European Office Action for Application No. 11730120.0, dated Oct. 21, 2014, 8 pages.
European Office Action for U.S. Appl. No. 14/165,153, dated Nov. 6, 2014, 6 pages.
European Office Action for U.S. Appl. No. 14/174,865, dated Sep. 2, 2014, 3 pages.
European Office Action for Application No. 14820267.4, dated May 4, 2017, 11 pages.
European Office Action for Application No. 17163411.6, dated Apr. 21, 2017, 8 pages.
European Office Action for Application No. 17163411.6, dated Aug. 6, 2018, 5 pages.
European Office Action for Application No. 17163411.6, dated Jun. 4, 2018, 8 pages.
European Office Action for Application No. 17163411.6, dated Oct. 8, 2018, 15 pages.
European Office Action for Application No. 19815783.6, dated Apr. 29, 2022, 14 pages.
European Office Action for Application No. 19815783.6, dated Jan. 28, 2022, 19 pages.
Indian Office Action for Application No. 8968/DELNP/2012, dated May 3, 2018, 7 pages.
International Preliminary Report on Patentability for Application No. PCT/US2005/029569, dated Feb. 20, 2007, 7 pages.
International Preliminary Report on Patentability for Application No. PCT/US2011/032641, dated Oct. 16, 2012, 19 pages.
International Search Report and Written Opinion for Application No. PCT/US2005/043980, dated Feb. 1, 2007.
International Search Report and Written Opinion for Application No. PCT/US2011/032641, dated Jan. 24, 2012, 24 pages.
International Search Report and Written Opinion for Application No. PCT/US2014/045457, dated Nov. 3, 2014, 11 pages.
International Search Report and Written Opinion for Application No. PCT/US2019/034962, dated Nov. 13, 2019, 25 pages.
International Written Opinion for Application No. PCT/US2005/029403, dated Apr. 13, 2006, 3 pages.
International Written Opinion for Application No. PCT/US2005/029407, dated Jun. 20, 2006, 3 pages.
International Written Opinion for Application No. PCT/US2005/029569, dated Oct. 19, 2006, 3 pages.
International Written Opinion for Application No. PCT/US2010/031407, dated Jun. 29, 2010, 7 pages.
Japanese Office Action for Application No. 2007-543322, dated Feb. 23, 2012.
Saudi Arabian Office Action for Application No. 520420679, dated Dec. 26, 2022, 9 pages.
US Office Action for U.S. Appl. No. 13/641,199, dated Feb. 8, 2016, 12 pages.
Japanese Office Action for Application No. 2022-117076, dated Aug. 4, 2023, 9 pages.

* cited by examiner

FIG. 5

ESKYGPPCPSCPAPEFLGGPSVFLFPPKPKD
TLMISRTPEVTCVVVDVSQEDPEVQFNWYV
DGVEVHNAKTKPREEQFNSTYRVVSVLTVLH
QDWLNGKEYKCKVSNKGLPSSIEKTISKAKG
QPREPQVYTLPPSQEEMTKNQVSLTCLVKG
FYPSDIAVEWESNGQPENNYKTTPPVLDSD
GSFFLYSRLTVDKSRWQEGNVFSCSVMHEA
LHNHYTQKSLSLSLG

FIG. 9A
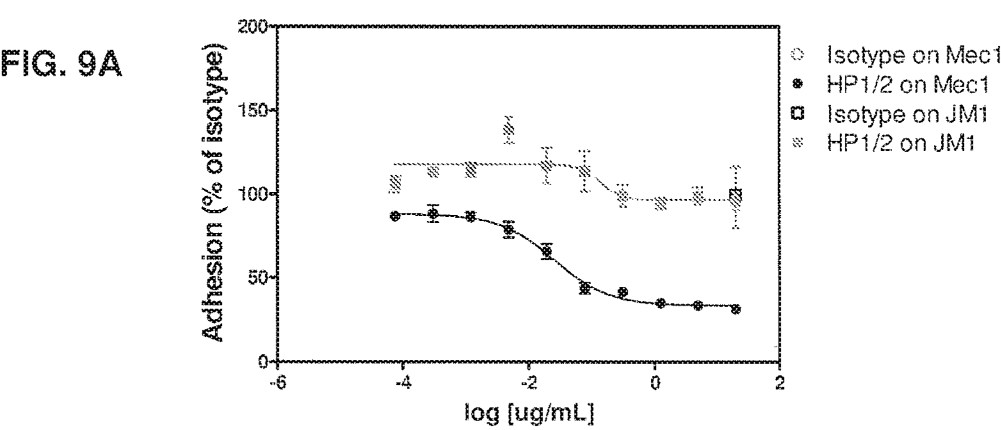
FIG. 9B
FIG. 9C
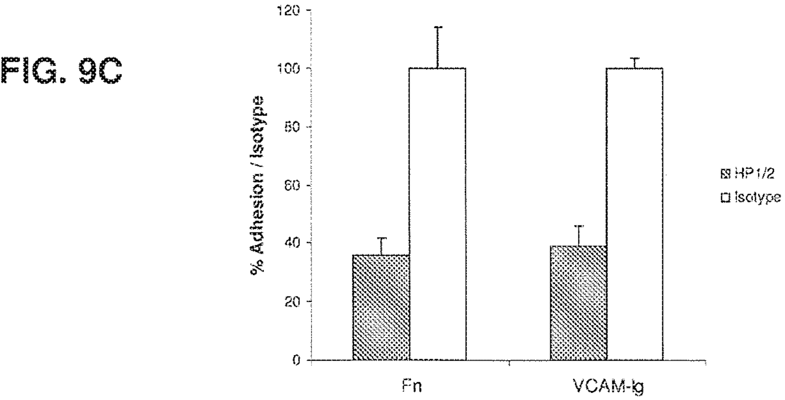

ANTI-VLA-4 ANTIBODIES

RELATED APPLICATIONS

This application is a Divisional of Ser. No. 17/366,903, filed Jul. 2, 2021, which is a Divisional of U.S. application Ser. No. 16/441,974, filed Jun. 14, 2019, now U.S. Pat. No. 11,083,791, which is a Continuation of U.S. application Ser. No. 15/838,884, filed Dec. 12, 2017, now U.S. Pat. No. 10,335,485, which is a Continuation of U.S. application Ser. No. 13/641,199, filed Nov. 25, 2013, which is a National Stage Application under 35 U.S.C. § 371 from PCT/US2011/032641, filed Apr. 15, 2011, and claims the benefit of U.S. Provisional Application No. 61/324,944, filed Apr. 16, 2010, each of which is incorporated herein by reference in its entirety.

FIELD OF THE INVENTION

This invention relates to alpha-4 binding antibodies, and fragments thereof.

SEQUENCE LISTING

The instant application contains a Sequence Listing which has been submitted in electronic format and is hereby incorporated by reference in its entirety. The name of the file containing the Sequence Listing is 123429 60106.xml. The size of the file is 19,772 bytes, and the file was created on Jun. 20, 2023.

BACKGROUND OF INVENTION

Humanized antibodies can be used as therapeutic agents in place of murine antibodies to avoid the undesirable immune response in humans termed the HAMA (Human Anti-Mouse Antibody) response. Humanized antibodies are generally constructed by replacing the complementary determining regions (CDRs) of a human antibody with the CDRs of another species, typically a mouse antibody.

VLA-4 (also called $\alpha4\beta1$) is a member of the $\beta1$ integrin family of cell surface receptors. VLA-4 contains an $\alpha4$ chain and a $\beta1$ chain and is involved in cell-cell interactions. Its expression is mainly restricted to lymphoid and myeloid cells. VLA-4 binds the endothelial cell ligand VCAM-1 (Vascular Cell Adhesion Molecule-1), and can mediate T and B lymphocyte attachment to the heparin II binding fragment of human plasma fibronectin.

SUMMARY OF INVENTION

The inventors have discovered that germline variable region frameworks can be used to optimize CDR-grafted alpha-4 binding antibodies, such as anti-VLA-4 antibodies. Accordingly, the invention features anti-VLA-4 variable heavy (VH) and variable light (VL) chains and antibody molecules including such frameworks.

In one aspect, the invention features an anti-$\alpha4$ antibody VH chain having CDRs from a donor anti-$\alpha4$ antibody, e.g., an anti-$\alpha4$ antibody described herein, and a VH framework having regions 1, 2, 3, and 4 from the sequence of, or having no more than 5, 10 or 15 differences from a germline variable region sequence for the VH chain. In one embodiment, variable framework region 4 (FR4) is a human consensus sequence. In one embodiment, the complete VH chain framework regions FR1, FR2, FR3 and FR4, are present. In another embodiment, the chain is an antigen-binding fragment of a VH region.

In one embodiment, the germline sequence is human IGHV1-f (SEQ ID NO:2), depicted in FIG. 1. In certain embodiments, the VH framework sequence can differ by at least one, but by no more than 2, 3, 4, 5, 10 or 15 amino acid residues from a germline sequence, e.g., SEQ ID NO:2. In one embodiment, the VH framework further includes other than the corresponding human residues. For example, the VH chain includes non-human residues, at one or more of framework positions 24, 67, 76, 80, and 94 (Kabat numbering) of SEQ ID NO:2.

In one embodiment, at least one or more of the complementary determining regions (CDRs) of the variable domains are derived from a donor non-human $\alpha4$-binding antibody. In one embodiment, the antigen binding regions of the CDR-grafted heavy chain variable domain include the CDRs corresponding to positions 26-34 (CDR1), 50-65 (CDR2) and 95-102 (CDR3) (Kabat numbering; Kabat et al., *Sequences of Proteins of Immunological Interest,* 5$^{th}$ ed., vol. 4, 1991, U.S. Department of Health and Human Services, NIH, USA).

Thus, in one embodiment, the variable heavy chain (VH) framework has an acceptor sequence derived from human antibody germline sequence IGHV1-f.

In another embodiment, at least one amino acid, and less than 2, 3, 4, 5, or 10 amino acid residues, in the FR1 region of the VH is other than the corresponding human germline residue. One or more of such residues can, for example, be identical to the nonhuman antibody framework region from which the CDR sequences are derived. In one embodiment, the amino acid residue at Kabat position 24 is mutated to be identical to the nonhuman antibody framework region.

In another embodiment, at least one amino acid, and less than 2, 3, 4, 5, or 10 amino acid residues, in the FR2 region of the VH is other than the corresponding human germline residue. One or more of such residues can, for example, be identical to the nonhuman antibody framework region from which the CDR sequences are derived.

In yet another embodiment, at least one amino acid, and less than 2, 3, 4, 5, or 10 amino acid residues, in FR3 of the VH chain is other than the corresponding human germline residue. One or more of such residues can, for example, be identical to the nonhuman antibody framework region from which the CDR sequences are derived. In one embodiment, the amino acid residue at Kabat position 94 is identical to the nonhuman antibody framework region. In yet another embodiment, the amino acid residues at Kabat positions 67, 76, 80, and 94 are identical to the nonhuman antibody framework region.

In certain embodiments, the VH chain of the antibody has the sequence of SEQ ID NO:3, SEQ ID NO:4, or SEQ ID NO:5.

In one aspect, the invention features, an anti-VLA-4 VL chain having CDRs from a donor anti-VLA-4 antibody, e.g., an anti-VLA-4 antibody described herein, and a VL framework having regions 1, 2, 3, and 4 from the sequence of, or having no more than 5, 10 or 15 differences (either per/region or in total) from, a germline variable region sequence for the VL chain. In one embodiment, variable framework region 4 (FR4) is a human consensus sequence. In one embodiment, the complete VL chain framework regions FR1, FR2, FR3 and FR4, are present. In another embodiment, the chain is an antigen-binding fragment of a VL region.

In another embodiment, the germline sequence is IGKV4-1 (SEQ ID NO:7), depicted in FIG. 2. In yet other embodiments, the VL framework sequence can differ by at least one, but no more than 2, 3, 4, 5, 10 or 15 amino acid residues from a germline framework sequence, e.g., SEQ ID NO:7. In another embodiment, the VL further includes other than the corresponding human amino acid residues. For example, the VL chain further includes non-human residues at one or more of framework positions 1, 73, and 87 (Kabat numbering) of SEQ ID NO:7.

In one embodiment, the sequence is AAH7035.1 (SEQ ID NO:12) or its germline engineered version (SEQ ID NO:13), depicted in FIG. 2. In some embodiments, the VL framework sequence can differ by at least one, but not more than 5, 10, 15, 20, or 25 amino acid residues from a germline engineered framework sequence, e.g., SEQ ID NO:13. In one embodiment, the VL chain includes other than the corresponding human residues. For example, the VL chain includes non-human residues at one or more of framework positions 1 and 87 (Kabat numbering) of SEQ ID NO:12. In another embodiment, the VL includes amino acid substitutions in the framework regions to resemble a different human germline framework sequence, such as from germline sequence IGKV4-1. In certain embodiments, the VL framework sequence is altered to be identical to the IGKV4-1 germline sequence at positions 1-3, 5-23, 35-37, 39-42, 45-49, 57, 59-61, 63-64, 70-72, 74-84,86-88, 99-106 (Kabat numbering) of SEQ ID NO:12.

In one embodiment, at least one or more of the complementary determining regions (CDRs) of the variable domains are derived from a donor non-human α4-binding antibody. In another embodiment, the antigen binding regions of the CDR-grafted heavy chain variable domain include the CDRs corresponding to positions 24-31 (CDR1), 50-56 (CDR2) and 89-97 (CDR3) (Kabat numbering). Thus, in one embodiment, the VL framework has an acceptor sequence constructed from IGKV4-1 germline sequence, from antibody AAH70335.1 or from germline engineered antibody AAH70335.1.

In yet another embodiment, at least one amino acid, and less than 2, 3, 4, 5, 10, or 15 residues, in FR1 of the VL chain is other than the corresponding human residue. One or more of such residues can, for example, be identical to the nonhuman antibody framework region from which the CDR sequences are derived. In one embodiment, the amino acid residue at the N-terminal position of FR1 is mutated to be identical to the nonhuman antibody framework region.

In another embodiment, at least one amino acid, and less than 2, 3, 4, 5, 10, or 15 residues, in FR2 of the VL chain is other than the corresponding human residue. One or more of such residues can, for example, be identical to the nonhuman antibody framework region from which the CDR sequences are derived.

In yet another embodiment, at least one amino acid, and less than 2, 3, 4, 5, 10, or 15 residues, in FR3 of the VL is other than the corresponding human residue. One or more of such residues can, for example, be identical to the nonhuman antibody framework region from which the CDR sequences are derived. In another embodiment, the amino acid residue at Kabat position 87 is mutated to be identical to the nonhuman antibody framework region. In yet another embodiment, the amino acid residues at Kabat positions 67 and 87 are mutated to be identical to the nonhuman antibody framework sequence. In yet another embodiment, the amino acid residues at Kabat positions 67, 73, and 87 of SEQ ID NO:7 are mutated to be identical to the nonhuman antibody framework sequence.

In other embodiments, the VL chain of the antibody has the sequence of SEQ ID NO:8, SEQ ID NO:9, SEQ ID NO:10, or SEQ ID NO:11.

In one embodiment, the CDRs of the VH and VL acceptor framework sequences are selected to resemble the CDR sequences of a nonhuman (e.g., murine) antibody sequence, where the nonhuman antibody binds integrin alpha-4 or a fragment thereof. In another embodiment, the sequences of the CDRs are selected to resemble the sequences of the CDRs of a non-human antibody that binds the B1 epitope of the VLA-4α4 chain. In one embodiment, the CDRs are selected to resemble a murine monoclonal antibody, e.g., HP1/2, HP2/1, HP2/4, L25, P4C2, or 21.6 (Pulido et al., J. Biol. Chem. 266:10241-10245, 1991; U.S. Pat. No. 6,033, 665). Modification can mean, e.g., excision and insertion or alteration, e.g., by directed mutagenesis.

In another aspect, the invention features an antibody, or antigen binding fragment thereof, including:

- an anti-VLA-4 VL chain described herein, e.g., an anti-VLA-4 VL chain having CDR's from a donor anti-VLA-4 antibody, e.g., an anti-VLA-4 antibody described herein, and a VL framework having LC framework regions 1, 2 and 3 from the sequence of, or having no more than 5, 10, or 15 differences from, a germline variable region sequence for the VL chain. In one embodiment, variable region 4 is a human consensus sequence; and
- an anti-VLA-4 VH chain described herein, e.g., an anti-VLA-4 VL chain having CDRs from a donor anti-VLA-4 antibody, e.g., an anti-VLA-4 antibody described herein, and a VL framework having LC framework regions 1, 2 and 3 from the sequence of, or having no more than 5, 10 or 15 differences from, a germline variable region sequence for the VL chain. In one embodiment, variable region 4 is a human consensus sequence.

In one embodiment, the antibody binds one or both of α4β1 and α4β7.

In another aspect, a VL or VH chain, or antibody, or fragment thereof, described herein is detectably labeled.

In yet another aspect, the invention features a vector containing DNA encoding an antibody heavy chain, or an α4 binding fragment thereof, described herein. In some embodiments, the DNA of the vector encodes a VH having the sequence of SEQ ID NO:3, SEQ ID NO:4, or SEQ ID NO:5.

In yet another aspect, the invention features a vector containing DNA encoding an antibody light chain, or an α4 binding fragment thereof, described herein. In some embodiments, the DNA of the vector encodes a VL chain having the sequence of SEQ ID NO:8, SEQ ID NO:9, SEQ ID NO:10 or SEQ ID NO:11.

In yet another aspect, the invention features a vector containing DNA encoding an antibody heavy chain, or an α4 binding fragment thereof, described herein and an antibody light chain, or an α4 binding fragment thereof, described herein.

In another aspect, the invention features a host cell containing a vector described herein, e.g., one capable of expressing a heavy and/or light chain antibody or antibody fragment described herein.

In one aspect, the invention features a method of making a recombinant anti-α4 antibody, or an α4-binding fragment thereof, by providing a host cell transfected with (a) a DNA sequence encoding an antibody heavy chain described herein, or an α4-binding fragment thereof, and (b) a DNA sequence encoding an antibody light chain, or an α4-binding fragment thereof, and culturing the transfected cell to produce the recombinant anti-α4 antibody molecule or α4 binding fragment thereof. The DNA encoding the antibody heavy and light chains can be produced on the same vector or on different vectors.

In one aspect, the invention features a method of making a recombinant anti-α4 antibody, or an α4-binding fragment thereof, by providing a host cell transfected with (a) a DNA sequence encoding an antibody heavy chain, or an α4-binding fragment thereof, e.g., where the DNA sequence has the sequence of SEQ ID NOs:3, 4, or 5, and (b) a DNA sequence encoding an antibody light chain, or an α4-binding fragment thereof, e.g., wherein the DNA sequence has the sequence of SEQ ID NOs: 8, 9, 10, or 11, and culturing the transfected cell line to produce the recombinant anti-α4 antibody molecule or α4 binding fragment thereof. The DNA encoding the antibody heavy and light chains can be produced on the same vector or on different vectors.

In another aspect, the invention features a method of treating a disease or disorder mediated by an α4 integrin, e.g., an α4131 (VLA-4) or α4137 integrin, by administering an α4 antibody or antibody fragment described herein, or a pharmaceutical composition containing the antibody or fragment, to a subject in need of such treatment. The subject can have or be at risk for developing, for example, inflammatory, immune, or autoimmune disorders (e.g., inflammation of the central nervous system, such as multiple sclerosis, meningitis, neuromyelitis optica, neurosarcoidosis, CNS vasculitis, encephalitis, and transverse myelitis), tissue or organ graft rejection or graft-versus-host disease, acute CNS injury, such as stroke, traumatic brain injury (TBI), or spinal cord injury (SCI); chronic renal disease; allergy, e.g., allergic asthma; type 1 diabetes mellitus; inflammatory bowel disorders, such as Crohn's disease, ulcerative colitis; myasthenia gravis; fibromyalgia; arthritic disorders, such as rheumatoid arthritis, psoriatic arthritis; inflammatory/immune skin disorders, such as psoriasis, vitiligo, dermatitis, lichen planus; systemic lupus erythematosus; Sjogren's Syndrome; hematological cancers, such as multiple myeloma, leukemia, lymphoma; solid cancers, such as sarcomas or carcinomas, e.g., of the lung, breast, prostate, brain; and fibrotic disorders, such as pulmonary fibrosis, myelofibrosis, liver cirrhosis, mesangial proliferative glomerulonephritis, crescentic glomerulonephritis, diabetic nephropathy, and renal interstitial fibrosis.

In another aspect, the invention features a method of treating a patient by administering to the patient an α4-binding antibody or antibody fragment. In one embodiment, the patient has a cancer, such as a solid tumor or a hematological malignancy. For example, a patient treated with an α4-binding antibody or antibody fragment can have acute myelogenous leukemia (AML) or multiple myeloma (MM).

In another embodiment, the patient has an inflammatory disorder, such as multiple sclerosis, asthma (e.g., moderate to severe asthma), rheumatoid arthritis, diabetes, or Crohn's disease. In another embodiment, the composition is administered as a regimen. In yet another embodiment, the method further includes selecting a patient suitable for treatment with the composition. A patient suitable for treatment, for example, has demonstrated a sign or symptom indicative of disease onset, such as a sign or symptom indicative of MS.

In yet another embodiment, the method further includes administering to the patient a second therapeutic agent, such as, a chemotherapeutic agent, a thrombolytic agent, a neuroprotective agent, an anti-inflammatory agent, a steroid, a cytokine, or a growth factor.

In one embodiment, the patient is administered a humanized anti-VLA-4 antibody, or fragment thereof, described herein, such as HuHP1/2, H1L1, H1L2 or H1L3.

In one embodiment, the composition containing an α4-binding antibody is administered as a regimen, such at regular intervals. For example, the composition can be administered once daily, weekly or monthly; once per week, twice per week, three times per week, four times per week or more; or once every two weeks, once every three weeks, once every four weeks or more.

In one embodiment, dosing can be adjusted according to a patient's rate of clearance of a prior administration of anti-α4 antibody. For example, in one embodiment, a patient will not be administered a second or follow-on dose before the level of anti-α4 antibodies in the patient's system has dropped below a pre-determined level. In one embodiment, a sample from a patient (e.g., plasma, serum, blood or urine sample) is assayed for the presence of anti-α4 antibodies, and if the level of anti-α4 antibodies is above a pre-determined level, the patient will not be administered a second or follow-on dose. If the level of anti-α4 antibodies in the patient's system is below a pre-determined level, then the patient is administered a second or follow-on dose.

In one embodiment, the composition is administered continuously, e.g., over a period of more than 30 minutes but less than 1, 2, 4, or 12 hours. The composition containing the antibody and the second agent can be administered by any appropriate method, e.g., subcutaneously, intramuscularly, or intravenously.

In some embodiments, each of the antibody and the second agent is administered at the same dose as each is prescribed for monotherapy. In other embodiments, the antibody is administered at a dosage that is equal to or less than an amount required for efficacy if administered alone. Likewise, the second agent can be administered at a dosage that is equal to or less than an amount required for efficacy if administered alone.

Another aspect featured in the disclosure is a method of evaluating a patient by determining if the patient meets a preselected criterion, and if the patient meets the preselected criterion approving, providing, prescribing, or administering a VLA-4 binding antibody formulation described herein to the patient. In one embodiment, the preselected criterion is the failure of the patient to adequately respond to a prior alternate therapeutic treatment or regimen, e.g., for treatment of MS. In another embodiment, the preselected criterion is the absence of any signs or symptoms of progressive multifocal leukoencephalopathy (PML), or the absence of any diagnosis of PML. In some cases, the selection is based on the absence of a risk factor for PML, for example, the subject does not test positive for JC virus DNA or does not test positive for JC virus antibodies. In another embodiment, the criterion is as described in PCT/US07/75577 (published as WO2008/021954), hereby incorporated by reference, which describes methods and systems for drug distribution and for providing drugs to patients.

In another aspect, a method of distributing a composition described herein is provided. The composition contains an alpha-4 binding antibody. The method includes providing a recipient (e.g., an end user, patient, physician, retail or wholesale pharmacy, distributor, or pharmacy department at a hospital, nursing home clinic or HMO) with a package containing sufficient unit dosages of the drug to treat a patient for at least 6, 12, 24, 36, or 48 months. In another aspect, the invention features a method of evaluating the quality of a package or lot of packages (e.g., to determine if it has expired) of a composition described herein containing an alpha-4 binding antibody. The method includes evaluating whether the package has expired. The expiration date is at least 6, 12, 24, 36, or 48 months, e.g., greater than 24 or 36 months, from a preselected event, such as manufacturing, assaying, or packaging. In some embodiments, a decision or step is taken as a result of the analysis. For example, depending on the right analysis, the antibody in the package is used or discarded, classified, selected, released or withheld, shipped, moved to a new location, released into commerce, sold, or offered for sale, withdrawn from commerce or no longer offered for sale, depending on whether the product has expired.

In another aspect, the invention features a package containing at least two unit doses of an aqueous composition containing an α4 binding antibody. In one embodiment, all of the unit doses contain the same amount of antibody, and in other embodiments there are unit dosages of two or more strengths, or two or more different formulations, e.g., having different strengths or release properties.

In another aspect, the invention includes a method of instructing a recipient on the administration of a formulation containing α4 binding antibody. The method includes instructing the recipient (e.g., an end user, patient, physician, retail or wholesale pharmacy, distributor, or pharmacy department at a hospital, nursing home clinic or HMO) that the antibody should be administered to a patient according to a regimen described herein. The method can also include instructing the recipient that the antibody should be administered prior to the expiration date. The expiration date is at least 6, 12, 24, 36, or 48 months, e.g., greater than 24 or 36 months, from a preselected event, such as manufacturing, assaying, or packaging. In one embodiment, the recipient also receives a supply of the antibody, e.g., a supply of unit dosages of the antibody.

In another aspect, the invention features a method of making an antibody which includes CDRs from a donor antibody, such as a non-human, e.g., a murine antibody, and one or both heavy and light chain variable region frameworks derived from human germline variable region framework region or regions. The method includes one or both of 1 and 2, where 1 and 2 are as follows:

1. identifying or selecting a stable human acceptor heavy chain variable framework which has the same residues as the non-human donor heavy chain at one or more of the residues in one or more of a), b) and c):
 a) VH Kabat #2, 4, 24, 26, 27, 29, 36, 38, 46, 47, 48, 49, 66, 67, 69, 71, 78, 93, and 94, which, without being bound by theory, are believed to be important for maintaining CDR conformations;
 b) VH Kabat #1, 2, 27, 28, 30, 43, 66, 68, 70, 72, 73, 74, and 75 which, without being bound by theory, are believed to be able to interact with antigen; and
 c) VH Kabat #37, 39, 44, 45, 47, 91, 93 and 103, which, without being bound by theory, are believed to be important for VH/VL interface integrity; and
2. identifying or selecting a stable acceptor light chain variable framework which has the same residues as the donor light chain at one or more of the residues in one or more of a), b) and c):
 a) VL Kabat #2, 4, 38, 43, 44, 48, 58, 64, 71, and 73, which without being bound by theory, are believed to be important for maintaining CDR conformations;
 b) VL Kabat #1, 2, 49, 57, 60, 63, 65, 66, 67, 68, 69, and 70 which without being bound by theory, are believed to potentially be able to interact with antigen; and
 c) VL Kabat #36, 38, 43, 44, 46, 49, 87, and 98, which without being bound by theory, are believed to be important for VH/VL interface integrity;
3. providing a variable region having donor CDRs and the selected germline framework having matched residues identified in 1 or 2, such as by selecting a germline sequence and further backmutating additional residues identified in 1 or 2 of the germline to murine sequence so as to further maximize matching at the residues identified in 1 and 2; and
4. evaluating each matched position, such as by 3D structural analysis or modeling, and if a position meets a predetermined standard for risk of, for example, interfering with CDR conformations, antigen interactions or VH/VL interface integrity, then reintroducing an equivalent murine residue, or a common human antibody residue, compatible with antibody structure.

In one embodiment, at least 3, 4 or 5 of the residues identified in (1.a) are matched. For example, in one embodiment, residues 24, 29, or 94 are matched.

In one embodiment, at least 3, 4 or 5 of the residues identified in (1.b) are matched. For example, in one embodiment, residues 1, 73, or 75 are matched.

In one embodiment, at least 3, 4 or 5 of the residues identified in (1.c) are matched. For example, in one embodiment, residues 37, 93, or 103 are matched.

In one embodiment, at least 3, 4 or 5 of the residues identified in (2.a) are matched. For example, in one embodiment, residues 2, 71 and 73 are matched.

In one embodiment, at least 3, 4 or 5 of the residues identified in (2.b) are matched. For example, in one embodiment, residues 1, 68, or 70 are matched.

In one embodiment, at least 3, 4 or 5 of the residues identified in (2.c) are matched. For example, in one embodiment, residues 46, 87, or 98 are matched.

In one embodiment, residue 6 in (1.a), residue 2 in (1.b), and residue 4 in (1.c) are matched.

In another embodiment, residue 4 in (2.a), residue 2 in (2.b), and residue 4 in (2.c) are matched.

In one embodiment, the heavy chain germline sequence is of VH3, VH1 and VH5 germline class. In another embodiment, the light chain germline sequence is a Vkappa or Vlambda sequence.

The term "treating" refers to administering a therapy in an amount, manner, and/or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the subject.

An "α4 binding antibody" refers to an antibody that binds to the α4 subunit of the VLA-4 (α4β1) integrin, and at least partially inhibits an activity of VLA-4, particularly a binding activity of a VLA-4 integrin or a signaling activity, e.g., ability to transduce a VLA-4 mediated signal. For example, a VLA-4 binding antibody may inhibit binding of VLA-4 to a cognate ligand of VLA-4, e.g., a cell surface protein such as VCAM-1 (Vascular Cell Adhesion Molecule-1), or to an extracellular matrix component, such as fibronectin or osteopontin. An alpha-4 binding antibody may bind to both α4β1 or α4β7. Typically, the antibody binds to the B1 epitope of α4. An α4 binding antibody may bind to VLA-4 with a $K_d$ of less than about $10^{-6}$, $10^{-7}$, $10^{-8}$, $10^{-9}$, $10^{-10}$, or $10^{-11}$ M.

As used herein, the term "antibody" refers to a protein that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The light chains of the immunoglobulin may be of types kappa or lambda. In one embodiment, the antibody is glycosylated. An antibody can be functional for antibody dependent cytotoxicity and/or complement-mediated cytotoxicity, or may be non-functional for one or both of these activities.

The VH and VL regions can be further subdivided into regions of hypervariability, termed "complementarity determining regions" ("CDR"), interspersed with regions that are more conserved, termed "framework regions" (FR). The extent of the FRs and CDRs has been precisely defined (see, Kabat, E. A., et al. (1991) *Sequences of Proteins of Immunological Interest*, Fifth Edition, U.S. Department of Health and Human Services, NIH Publication No. 91-3242; and Chothia, C. et al. (1987) J. Mol. Biol. 196:901-917). Kabat definitions are used herein. Each VH and VL is typically composed of three CDRs and four FRs, arranged from amino-terminus to carboxyl-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay (1988) Ann. Rev. Immunol. 6:381-405).

As used herein, an "immunoglobulin variable domain sequence" refers to an amino acid sequence that can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with VLA-4.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2 and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system.

The term "immunoglobulin" comprises various broad classes of polypeptides that can be distinguished biochemically. Those skilled in the art will appreciate that heavy chains are classified as gamma, mu, alpha, delta, or epsilon (γ, α, δ, ε) with some subclasses among them (e.g., γ1-γ4). It is the nature of this chain that determines the "class" of the antibody as IgG, IgM, IgA IgD, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention. Light chains are classified as either kappa or lambda (κ, λ). Each heavy chain class may be bound with either a kappa or lambda light chain.

The term "antigen-binding fragment" of a full length antibody refers to one or more fragments of a full-length antibody that retain the ability to specifically bind to a target of interest, e.g., VLA-4. Examples of binding fragments encompassed within the term "antigen-binding fragment" of a full length antibody include (i) a Fab fragment, a monovalent fragment consisting of the VL, VH, CL and CH1 domains; (ii) a $F(ab')_2$ fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) Science 242:423-426; and Huston et al. (1988) Proc. Natl. Acad. Sci. USA 85:5879-5883.

In some embodiments, the above-described antibodies are pegylated.

In some embodiments, the above-described antibodies or fragments thereof are multispecific. In further embodiments, the above-described antibodies or fragments thereof are monovalent or bispecific.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 5 is the amino acid sequence of an IgG4 Fc (hinge+CH2+CH3 domain). The hinge region is depicted in bold, and the CH3 domain is underlined. The boxed "S" is Ser228. The circled "N" is Asn297.

FIG. 7A depicts inhibition of binding of HL60 and KG1 cells to FN-coated wells. FIG. 7B depicts inhibition of binding of KG1 cells to VCAM1-Ig-coated wells. FIG. 7C depicts inhibition of binding of HL60 cells to FN- and VCAM1-Ig-coated wells when incubated with 20 μg/mL HuHP1/2 (Solid bars). Clear bars indicate percent cell adhesion in the presence of an isotype control. "HP1/2" refers to humanized HP1/2.

FIG. 8A depicts inhibition of binding of U266 and H929 cells to FN-coated wells. FIG. 8B depicts inhibition of binding of U266 and H929 cells to VCAM1-Ig-coated wells. FIG. 8C depicts inhibition of binding of U266 cells to FN- and VCAM1-Ig-coated wells when incubated with 20 μg/mL HuHP1/2 (Solid bars). Clear bars indicate percent cell adhesion in the presence of an isotype control. "HP1/2" refers to humanized HP1/2.

FIGS. 9A-9C makes up a panel of graphs depicting inhibition of binding of CLL cell lines to fibronectin or VCAM1-Ig coated wells by HuHP1/2. FIG. 9A depicts inhibition of binding of Mec1 and JM1 cells to FN-coated wells. FIG. 9B depicts inhibition of binding of Mec1 and JM1 cells to VCAM1-Ig-coated wells. FIG. 9C depicts inhibition of binding of Mec1 cells to FN- and VCAM1-Ig-coated wells when incubated with 20 μg/mL HuHP1/2 (Solid bars). Clear bars indicate percent cell adhesion in the presence of an isotype control. "HP1/2" refers to humanized HP1/2.

DETAILED DESCRIPTION

Figure 1:
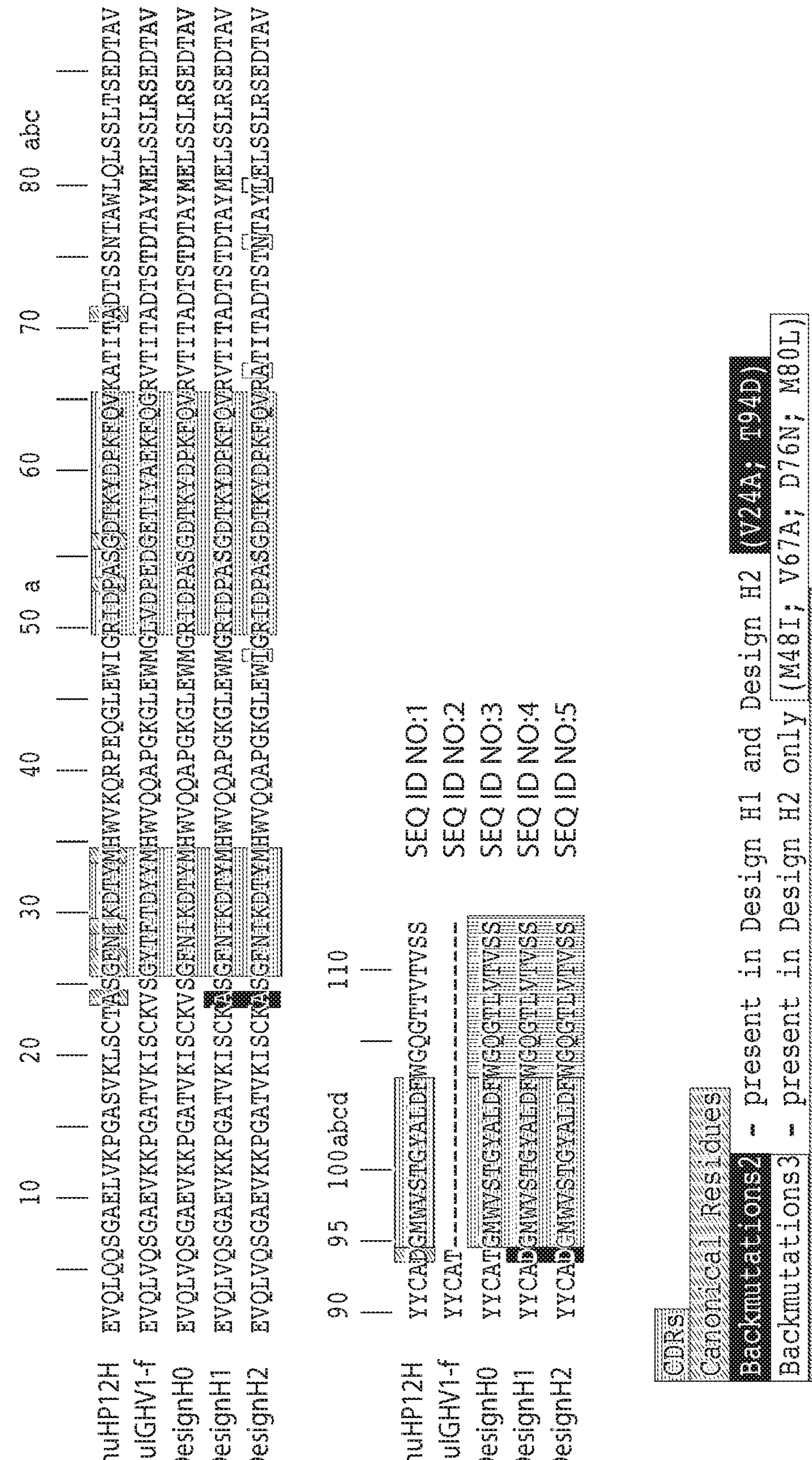
FIG. 1 displays the three sequence variants of HP1/2 heavy chain to a human heavy germline IGHV1-f. The lower case letters above the sequence represent insertions according to the Kabat numbering scheme.

Antibodies against VLA-4 have been demonstrated to be useful in treating disease. For example, natalizumab (Tysabri®), an anti-VLA-4 antibody is used for treating relapsing multiple sclerosis and Crohn's disease. However, for treatment of certain conditions, for example acute conditions such as spinal cord injury (SCI) or traumatic brain injury (TBI), or treatments that are administered in a finite number such as treatment of cancer, it may be advantageous to treat with an anti-VLA-4 antibody that binds with an affinity different than natalizumab, e.g., a higher affinity. In addition, treatment with anti-VLA-4 antibodies is associated with a rare but sometimes fatal disorder, progressive multifocal leukoencephalopathy (PML), for which a part of the treatment requires removal of antibody from the treated subject, for example using plasma exchange or immunoabsorption. Because of the need to remove antibody, it is also desirable to balance the advantages of an antibody that has increased affinity for VLA-4 with the disadvantage of an antibody that binds so tightly as to make removal difficult or to create a risk associated with a slow turnover rate. Such antibodies may also be useful for treating conditions such as multiple sclerosis in that less frequent treatment may be required or administration by means other than infusion may be more efficient. Enabling treatment with lower doses may also lower the risk of adverse events such as PML. Accordingly, the present invention provides antibodies having such desirable properties.

The invention is based at least in part on the unexpected characteristics of newly designed humanized α4-binding antibodies that have a binding affinity for α4 that is 10-fold higher than that of the anti-α4 antibody natalizumab.

Alpha-4 binding antibodies, and fragments thereof, are provided where the variable light chain (VL) and variable heavy chain (VH) frameworks have acceptor sequences constructed from germline or germline engineered antibody sequences, such as IGKV4-1 or geAAH70335.1 or IGHV1-f antibodies. The CDR sequences are derived from nonhuman anti-α4 binding antibodies such as the anti-VLA-4 antibody HP1/2. Antibodies described herein can have an increase of at least 1.5, 2.0, 2.5, 3.0 fold in affinity, e.g., relative to its murine parent. In one embodiment, the increase in affinity is at least 1.5, 2.0, 2.5, 3.0 fold but is respectively, less than 25, 20, or 15 fold.

Pharmaceutical Compositions

An α4 binding agent, such as a VLA-4 binding antibody, can be formulated as a pharmaceutical composition. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The antibody compositions described herein can be formulated according to methods known in the art. Pharmaceutical formulation is a well-established art, and is further described in Gennaro (ed.), *Remington: The Science and Practice of Pharmacy,* 20$^{th}$ ed., Lippincott, Williams & Wilkins (2000) (ISBN: 0683306472); Ansel et al., *Pharmaceutical Dosage Forms and Drug Delivery Systems,* 7$^{th}$ Ed., Lippincott Williams & Wilkins Publishers (1999) (ISBN: 0683305727); and Kibbe (ed.), *Handbook of Pharmaceutical Excipients American Pharmaceutical Association,* 3$^{rd}$ ed. (2000) (ISBN: 091733096X).

In one embodiment, the α4 antibody can be formulated with excipient materials, such as sodium chloride, sodium dibasic phosphate heptahydrate, sodium monobasic phosphate, and polysorbate 80. In another embodiment, the α4 antibody can be formulated in a citrate buffer, e.g., at pH 5, 5.5, 6, 6.5, 7, or 7.5. In yet another embodiment, the α4 antibody can be formulated in a solution including 2, 4, 5, 6, 8, 10, 12, 14, or 15% sucrose. It can be provided, for example, in a buffered solution at a concentration of about 20 mg/ml and can be stored at 2-8° C.

Pharmaceutical compositions may also be in a variety of other forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Typically, compositions for the agents described herein are in the form of injectable or infusible solutions.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Pharmaceutical compositions typically must be sterile and stable under the conditions of manufacture and storage. A pharmaceutical composition can also be tested to insure it meets regulatory and industry standards for administration.

The composition can be formulated as a solution, microemulsion, dispersion, liposome, or other ordered structure suitable to high drug concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

Administration

An α4 binding antibody can be administered to a subject, e.g., a human subject, by a variety of methods. For many applications, the route of administration is one of: intravenous injection or infusion, subcutaneous injection, or intramuscular injection. An α4 binding antibody can be administered as a fixed dose, or in a mg/kg dose. The antibody can be administered intravenously (IV) or subcutaneously (SC). For example, the antibody can be administered at a fixed unit dose of between about 50-600 mg IV, e.g., every 4 weeks, or between about 50-100 mg SC (e.g., 75 mg), e.g., at least once a week (e.g., twice a week). In one embodiment, the antibody is administered IV at a fixed unit dose of 50 mg, 60 mg, 80 mg, 100 mg, 120 mg, 130 mg, 140 mg, 150 mg, 160 mg, 180 mg, 200 mg, 300 mg, 400 mg, 500 mg, or 600 mg or more. Administration of the IV dose can be once or twice or three times or more per week, or once every two, three, four, or five weeks, or less frequently.

In one embodiment, the antibody is administered SC at a fixed unit dose of 50 mg, 60 mg, 70 mg, 75 mg, 80 mg, 100 mg, or 120 mg or more. Administration of the SC dose can be once or twice or three times or more per week, or once every two, three, four, or five weeks, or less frequently.

An anti-α4 antibody can also be administered in a bolus at a dose of between about 1 and 10 mg/kg, e.g., about 6.0 mg/kg, 4.0 mg/kg, 3.0 mg/kg, 2.0 mg/kg, 1.0 mg/kg. Modified dose ranges include a dose that is less than about 600 mg/subject, about 400 mg/subject, about 300 mg/subject, about 250 mg/subject, about 200 mg/subject, or about 150 mg/subject, typically for administration every fourth week or once a month. The α4 binding antibody can be administered, for example, every three to five weeks, e.g., every fourth week, or monthly.

Dosing can be adjusted according to a patient's rate of clearance of a prior administration of anti-α4 antibody. For example, a patient may not be administered a second or follow-on dose before the level of anti-α4 antibodies in the patient's system has dropped below a pre-determined level. In one embodiment, a sample from a patient (e.g., plasma, serum, blood, urine, or cerebrospinal fluid (CSF)) is assayed for the presence of anti-α4 antibodies, and if the level of anti-α4 antibodies is above a pre-determined level, the patient will not be administered a second or follow-on dose. If the level of anti-α4 antibodies in the patient's system is below a pre-determined level, then the patient is administered a second or follow-on dose. A patient whose anti-α4 levels are determined to be too high (above the pre-determined level) can be tested again after one or two or three days, or a week, and if the level of anti-α4-antibody in the patient samples has dropped below the pre-determined level, the patient may be administered a second or follow-on dose of antibody.

The dose can also be chosen to reduce or avoid production of antibodies against the α4 binding antibody, to achieve greater than 40, 50, 70, 75, or 80% saturation of the α4 subunit, to achieve less than 80, 70, 60, 50, or 40% saturation of the α4 subunit, or to prevent an increase in the level of circulating white blood cells In certain embodiments, the active agent may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Controlled Drug Delivery* (*Drugs and the Pharmaceutical Sciences*), Second Edition, J. Robinson and V. H. L. Lee, eds., Marcel Dekker, Inc., New York, 1987.

Pharmaceutical compositions can be administered with a medical device. For example, pharmaceutical compositions can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules are discussed in, e.g., U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Of course, many other such implants, delivery systems, and modules are also known.

This disclosure also features a device for administering a first and second agent. The device can include, for example, one or more housings for storing pharmaceutical preparations, and can be configured to deliver unit doses of the first and second agent. The first and second agents can be stored in the same or separate compartments. For example, the device can combine the agents prior to administration. It is also possible to use different devices to administer the first and second agent.

Dosage regimens are adjusted to provide the desired response, such as a therapeutic response or a combinatorial therapeutic effect. Generally, any combination of doses (either separate or co-formulated) of the VLA-4 binding agent and the second agent can be used in order to provide a subject with both agents in bioavailable quantities.

Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with the other agent.

A pharmaceutical composition may include a "therapeutically effective amount" of an agent described herein. Such effective amounts can be determined based on the combinatorial effect of the administered first and second agent. A therapeutically effective amount of an agent may also vary according to factors such as the disease state, age, sex, and weight of the individual, and the ability of the compound to elicit a desired response in the individual, such as amelioration of at least one disorder parameter, e.g., a multiple sclerosis parameter, or amelioration of at least one symptom of the disorder, e.g., a symptom of multiple sclerosis, such as muscle atrophy, ataxia, and tremors. A therapeutically effective amount is also one in which any toxic or detrimental effects of the composition are outweighed by the therapeutically beneficial effects.

Devices and Kits

Formulations containing an antibody described herein can be administered with a medical device. The device can be designed with features such as portability, room temperature storage, and ease of use so that it can be used in emergency situations, such as by an untrained subject or by emergency personnel in the field, removed to medical facilities and other medical equipment. The device can include, for example, one or more housings for storing pharmaceutical preparations that include an α4-binding antibody, and can be configured to deliver one or more unit doses of the agent.

For example, the pharmaceutical composition can be administered with a transcutaneous delivery device, such as a syringe, including a hypodermic or multichamber syringe. Other suitable delivery devices include stents, catheters, microneedles, and implantable controlled release devices. The composition can be administered intravenously with standard IV equipment, including, e.g., IV tubings, with or without in-line filters. In certain embodiments, the device will be a syringe for use in SC or IM administration.

Pharmaceutical compositions can be administered with medical devices. For example, pharmaceutical compositions can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules are described in, e.g., U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. The therapeutic composition can also be in the form of a biodegradable or nonbiodegradable sustained release formulation for subcutaneous or intramuscular administration. Methods for such compositions are known in the art. Continuous administration can also be achieved using an implantable or external pump. The administration can also be conducted intermittently, such as by single daily injection, or continuously at a low dose, such as in a sustained release formulation. The delivery device can be modified to be optimally suited for administration of an α4-binding antibody. For example, a syringe can be siliconized to an extent that is optimal for storage and delivery of the antibody. Of course, many other such implants, delivery systems, and modules are also known.

This disclosure also features a device for administering a first and second agent (e.g., an antibody and a second agent). The device can include, for example, one or more housings for storing pharmaceutical preparations, and can be configured to deliver unit doses of the first and second agent. The first and second agents can be stored in the same or separate compartments. In one embodiment, the device combines the agents prior to administration. In some embodiments, the first and second agents are administered by different devices.

An α4-binding antibody can be provided in a kit. In one embodiment, the kit includes (a) a container that contains a composition that includes a high concentration of VLA-4-binding antibody, optionally (b) a container that contains a composition that includes a second agent, and optionally (c) informational material. The informational material can be descriptive, instructional, marketing or other material that relates to the methods described herein and/or the use of the agents for therapeutic benefit. In one embodiment, the kit also includes a second agent. For example, the kit includes a first container that contains a composition that includes the α4-binding antibody, and a second container that includes the second agent.

The informational material of the kits is not limited in its form. In one embodiment, the informational material can include information about production of the antibody, concentration, date of expiration, batch or production site information, and so forth. In one embodiment, the informational material relates to methods of administering the α4-binding antibody, e.g., in a suitable dose, dosage form, or mode of administration (e.g., a dose, dosage form, or mode of administration described herein), to treat a subject who has an acute disorder such as a spinal cord injury or traumatic brain injury, or an inflammatory disease (e.g., MS), or who is at risk for experiencing an episode associated with an inflammatory disease. The information can be provided in a variety of formats, including printed text, computer readable material, video recording, or audio recording, or information that provides a link or address to substantive material.

In addition to the agent, the composition in the kit can include other ingredients, such as a solvent or buffer, a stabilizer, or a preservative. The agent can be provided in any form, e.g., liquid, dried or lyophilized form, and substantially pure and/or sterile. When the agents are provided in a liquid solution, the liquid solution typically is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the α4 binding antibody and the second agent, such as in a desired ratio. For example, the kit can include a plurality of syringes, ampoules, foil packets, blister packs, or medical devices each containing, for example, a single combination unit dose. The containers of the kits can be air tight, waterproof (e.g., impermeable to changes in moisture or evaporation), and/or light-tight.

The kit optionally includes a device suitable for administering the composition, e.g., a syringe or other suitable delivery device. The device can be provided pre-loaded with one or both of the agents or can be empty but suitable for loading.

Oncology

The α4-binding antibodies and methods described herein can be used to treat cancer, including solid cancers and hematological malignancies. Exemplary solid cancers include sarcomas and carcinomas, such as of the lung, breast, pancreas, colon, prostate, bladder and brain. Hematological malignancies include cancers such as multiple myeloma, leukemia, and lymphoma.

Methods are provided for treating a patient having a hematological malignancy with a composition containing an α4-binding antibody, such as anti-VLA-4 antibody described herein. Hematological malignancies are cancers of the body's blood-forming and immune systems. Cancers of this type affect the blood, bone marrow, and/or lymph nodes. Hematological malignancies include leukemias, such as acute lymphoblastic leukemia (ALL), acute myelogenous leukemia (AML), chronic myelogenous leukemia (CML), chronic lymphocytic leukemia (CLL), acute promyelocytic leukemia, acute erythroleukemia, and hairy cell leukemia (HCL); lymphomas, such as Hodgkin's disease and Non-Hodgkin's lymphoma; and multiple myeloma; Waldenstrom's macroblobulinemia; myelodysplastic syndrome (MDS) (which can culminate in AML); a myeloproliferative disease, such as polycythemia vera (also called PV, PCV or polycythemia rubra vera (PRV)), Essential thrombocytosis (ET), myelofibrosis, heavy chain disease; and amyloid due to light-chain disease.

Patients having a hematological malignancy may be identified by analysis of blood count and blood film by, for example, light microscopy, which is useful for identifying malignant cells. A biopsy, such as from bone marrow, can also be used to identify malignant cells, and a biopsy from a lymph node can be useful for identifying a lymphadenopathy.

An α4-binding antibody (e.g., a humanized anti-VLA-4 antibody, such as HuHP1/2, H1L0, H1L1, H1L2 or H1L3) is useful for the treatment of a leukemia, such as AML. Leukemias are cancers that originate in the bone marrow, where the malignant cells are white blood cells (leukocytes). AML (also called acute myelocytic leukemia, acute myeloblastic leukemia, acute granulocytic leukemia, and acute nonlymphocytic leukemia) is a malignancy that arises in either granulocytes or monocytes. AML is characterized by the uncontrolled, exaggerated growth and accumulation of cells called leukemic blasts, which fail to function as normal blood cells, and the blockade of the production of normal marrow cells, leading to a deficiency of red cells (anemia), and platelets (thrombocytopenia) and normal white cells (especially neutrophils, i.e., neutropenia) in the blood.

All subtypes of AML are suitable for treatment with a VLA-4 binding antibody. The subtypes of AML are classified based on the stage of development myeloblasts have reached at the time of diagnosis. The categories and subsets allow the physician to decide what treatment works best for the cell type and how quickly the disease may develop. The subsets are: M0, myeloblastic, on special analysis; M1, Myeloblastic, without maturation; M2, Myeloblastic, with maturation; M3, Promyelocytic; M4, Myelomonocytic; M5, Monocytic; M6, Erythroleukemia; and M7, Megakaryocytic. A VLA-4 antibody can be administered with a secondary agent that is particularly suited to the subtype of AML. For example, acute promyelocytic leukemia (APL) and acute monocytic leukemia are subtypes of AML that need different treatment than other subtypes of AML. A second agent for treatment of APL can include all-trans retinoic acid (ATRA) or an antimetabolite, such as cytarabine. A second agent for treatment of acute monocytic leukemia can include a deoxyadenosine analog, such as 2-chloro-2'-deoxyadenosine (2-CDA).

Risk factors of AML include the presence of certain genetic disorders, such as Down syndrome, Fanconi anemia, Shwachman-Diamond syndrome and others. A patient having AML and a genetic disorder can be administered a VLA-4 binding antibody and a second agent to treat a symptom of the genetic disorder. For example, a patient with AML and Fanconi anemia can be administered a VLA-4 binding antibody and an antibiotic.

Other risk factors for AML include chemotherapy or radiotherapy for treatment of a different cancer, tobacco smoke, and exposure to large amounts of benzene.

Other cancers suitable for treatment with an α4-binding antibody include, solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, ovarian cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, small cell lung carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma).

Other Disorders

The formulations and methods described herein can also be used to treat other inflammatory, immune, or autoimmune disorders, e.g., inflammation of the central nervous system (e.g., in addition to multiple sclerosis, meningitis, neuromyelitis optica, neurosarcoidosis, CNS vasculitis, encephalitis, and transverse myelitis); tissue or organ graft rejection or graft-versus-host disease; acute CNS injury, e.g., stroke or spinal cord injury (SCI); chronic renal disease; allergy, e.g., allergic asthma, moderate to severe allergic rhinitis, ocular allergy; type 1 diabetes mellitus; inflammatory bowel disorders, e.g., Crohn's disease, ulcerative colitis (e.g., for treatment or maintenance of remission); eosinophilic gastroenteritis; myasthenia gravis; fibromyalgia; disorders associated with rheumatology/immunology, such as arthritic disorders, e.g., rheumatoid arthritis, psoriatic arthritis; dermatological disorders, such as inflammatory/immune skin disorders, e.g., psoriasis, vitiligo, dermatitis (e.g., atopic dermatitis), lichen planus, moderate to severe chronic urticaria; systemic lupus erythematosus (SLE; e.g., lupus nephritis); scleroderma (e.g., Progressive Systemic Sclerosis (PSS), such as PSS of the lung); acute or chronic primary eosinophilic pneumonia; Sjogren's Syndrome; acute coronary syndrome (ACS); acute myocardial infarction; atherosclerosis; and fibrotic disorders, e.g., pulmonary fibrosis (e.g., idiopathic pulmonary fibrosis), lung fibrosis (e.g., XRT induced), myelofibrosis, liver cirrhosis, mesangial proliferative glomerulonephritis, crescentic glomerulonephritis, diabetic nephropathy, and renal interstitial fibrosis.

The formulations and methods described herein can also be used to treat neurological disorders, such as cerebral ischemia, including prevention in patients with transient ischemic attacks and/or arterial stenosis. Other exemplary neurological disorders include chronic inflammatory demyelinating polyneuropathy (CIDP); Guillian-Barre Syndrome (GBS); ocular diseases, such as macular degeneration (e.g., wet macular degeneration), and anteriorischemic optic neuropathy; neuropathic pain (e.g., symptomatic neuropathic pain); Alzheimer's Disease; Amyotrophic Lateral Sclerosis (ALS) (e.g., disease modifying ALS)' and Parkinson's Disease.

The formulations and methods described herein can also be used to treat patients who have undergone transplantation, such as renal, heart, or bone marrow transplantation.

Multiple Sclerosis

Formulations containing an alpha-4 binding antibody described herein are useful for the treatment of inflammatory diseases, such as multiple sclerosis (MS). Multiple sclerosis is a central nervous system disease that is characterized by inflammation and loss of myelin sheaths.

Patients having MS may be identified by criteria establishing a diagnosis of clinically definite MS as defined by the workshop on the diagnosis of MS (Poser et al., Ann. Neurol. 13:227, 1983). For example, an individual with clinically definite MS has had two attacks and clinical evidence of either two lesions or clinical evidence of one lesion and paraclinical evidence of another, separate lesion. Definite MS may also be diagnosed by evidence of two attacks and oligoclonal bands of IgG in cerebrospinal fluid or by combination of an attack, clinical evidence of two lesions and oligoclonal band of IgG in cerebrospinal fluid. The McDonald criteria can also be used to diagnose MS. (McDonald et al., 2001, "Recommended diagnostic criteria for multiple sclerosis: guidelines from the International Panel on the Diagnosis of Multiple Sclerosis," *Ann. Neurol.* 50:121-127). The McDonald criteria include the use of MRI evidence of CNS impairment over time to be used in diagnosis of MS, in the absence of multiple clinical attacks. Effective treatment of multiple sclerosis may be evaluated in several different ways. The following parameters can be used to gauge effectiveness of treatment. Two exemplary criteria include: EDSS (extended disability status scale), and appearance of exacerbations on MRI (magnetic resonance imaging). The EDSS is a method for grading clinical impairment due to MS (Kurtzke, Neurology 33:1444, 1983). Eight functional systems are evaluated for the type and severity of neurologic impairment. Briefly, prior to treatment, patients are evaluated for impairment in the following systems: pyramidal, cerebella, brainstem, sensory, bowel and bladder, visual, cerebral, and other. Follow-ups are conducted at defined intervals. The scale ranges from 0 (normal) to 10 (death due to MS). A decrease of one full step indicates an effective treatment (Kurtzke, *Ann. Neurol.* 36:573-79, 1994). Patients may also be diagnosed using other criteria used by those in the art.

Exacerbations are defined as the appearance of a new symptom that is attributable to MS and accompanied by an appropriate new neurologic abnormality (IFNB MS Study Group, supra). In addition, the exacerbation must last at least 24 hours and be preceded by stability or improvement for at least 30 days. Briefly, patients are given a standard neurological examination by clinicians. Exacerbations are either mild, moderate, or severe according to changes in a Neurological Rating Scale (Sipe et al., *Neurology* 34:1368, 1984). An annual exacerbation rate and proportion of exacerbation-free patients are determined.

Therapy can be deemed to be effective if there is a statistically significant difference in the rate or proportion of exacerbation-free or relapse-free patients between the treated group and the placebo group for either of these measurements. In addition, time to first exacerbation and exacerbation duration and severity may also be measured. A measure of effectiveness as therapy in this regard is a statistically significant difference in the time to first exacerbation or duration and severity in the treated group compared to control group. An exacerbation-free or relapse-free period of greater than one year, 18 months, or 20 months is particularly noteworthy. Efficacy may also be assessed using any method used in the art, for example to assess symptoms of MS, including mobility improvement using a timed walk test used alone or in combination with other criteria, Efficacy of administering a first agent and, optionally, a second agent, can also be evaluated based on one or more of the following criteria: frequency of MBP reactive T cells determined by limiting dilution, proliferation response of MBP reactive T cell lines and clones, cytokine profiles of T cell lines and clones to MBP established from patients. Efficacy is indicated by decrease in frequency of reactive cells, a reduction in thymidine incorporation with altered peptide compared to native, and a reduction in TNF and IFN-$\alpha$.

Clinical measurements include the relapse rate in one and two-year intervals, and a change in EDSS, including time to progression from baseline of 1.0 unit on the EDSS that persists for six months. On a Kaplan-Meier curve, a delay in sustained progression of disability shows efficacy. Other criteria include a change in area and volume of T2 images on MRI, and the number and volume of lesions determined by gadolinium enhanced images.

MRI can be used to measure active lesions using gadolinium-DTPA-enhanced imaging (McDonald et al. *Ann. Neurol.* 36:14, 1994) or the location and extent of lesions using $T_2$-weighted techniques. Briefly, baseline MRIs are obtained. The same imaging plane and patient position are used for each subsequent study. Positioning and imaging sequences can be chosen to maximize lesion detection and facilitate lesion tracing. The same positioning and imaging sequences can be used on subsequent studies. The presence, location and extent of MS lesions can be determined by radiologists. Areas of lesions can be outlined and summed slice by slice for total lesion area. Three analyses may be done: evidence of new lesions, rate of appearance of active lesions, percentage change in lesion area (Paty et al., Neurology 43:665, 1993). Improvement due to therapy can be established by a statistically significant improvement in an individual patient compared to baseline or in a treated group versus a placebo group.

Exemplary symptoms associated with multiple sclerosis, which can be treated with the methods described herein, include: optic neuritis, diplopia, nystagmus, ocular dysmetria, internuclear ophthalmoplegia, movement and sound phosphenes, afferent pupillary defect, paresis, monoparesis, paraparesis, hemiparesis, quadraparesis, plegia, paraplegia, hemiplegia, tetraplegia, quadraplegia, spasticity, dysarthria, muscle atrophy, spasms, cramps, hypotonia, clonus, myoclonus, myokymia, restless leg syndrome, footdrop, dysfunctional reflexes, paraesthesia, anaesthesia, neuralgia, neuropathic and neurogenic pain, l'hermitte's, proprioceptive dysfunction, trigeminal neuralgia, ataxia, intention tremor, dysmetria, vestibular ataxia, vertigo, speech ataxia, dystonia, dysdiadochokinesia, frequent micturation, bladder spasticity, flaccid bladder, detrusor-sphincter dyssynergia, erectile dysfunction, anorgasmy, frigidity, constipation, fecal urgency, fecal incontinence, depression, cognitive dysfunction, dementia, mood swings, emotional lability, euphoria, bipolar syndrome, anxiety, aphasia, dysphasia, fatigue, uhthoff's symptom, gastroesophageal reflux, and sleeping disorders.

Each case of MS displays one of several patterns of presentation and subsequent course. Most commonly, MS first manifests itself as a series of attacks followed by complete or partial remissions as symptoms mysteriously lessen, only to return later after a period of stability. This is called relapsing-remitting (RR) MS. Primary-progressive (PP) MS is characterized by a gradual clinical decline with no distinct remissions, although there may be temporary plateaus or minor relief from symptoms. Secondary-progressive (SP) MS begins with a relapsing-remitting course followed by a later primary-progressive course. Rarely, patients may have a progressive-relapsing (PR) course in which the disease takes a progressive path punctuated by acute attacks. PP, SP, and PR are sometimes lumped together and called chronic progressive MS.

A few patients experience malignant MS, defined as a swift and relentless decline resulting in significant disability or even death shortly after disease onset. This decline may be arrested or decelerated by administration of a combination therapy described herein.

Administration of an anti-$\alpha 4$ antibody featured herein can be effective to relieve one or more symptoms of MS, such as one or more of the symptoms described above. For example, administration of an anti-$\alpha 4$ antibody described herein can be used to treat primary or secondary progressive multiple sclerosis (PPMS or SPMS, respectively), and treatment with an anti-$\alpha 4$ antibody can be effective to prevent relapse.

In addition to or prior to human studies, an animal model can be used to evaluate the efficacy of using the two agents. An exemplary animal model for multiple sclerosis is the experimental autoimmune encephalitis (EAE) mouse model, e.g., as described in (Tuohy et al. (J. Immunol. (1988) 141: 1126-1130), Sobel et al. (J. Immunol. (1984) 132: 2393-2401), and Traugott (Cell Immunol. (1989) 119: 114-129). Mice can be administered a first and second agent described herein prior to EAE induction. Then the mice are evaluated for characteristic criteria to determine the efficacy of using the two agents in the model.

Antibody Generation

Recombinant antibodies that bind to alpha-4 can be generated by in vivo or in vitro methods such as phage display. The methods can be used to supply anti-$\alpha 4$ CDRs for use in CDR grafted antibodies described herein. In addition, methods such as phage display can be used to select such CDRs in the context of the germline frameworks disclosed herein, such as by using a library where the framework is a germline framework.

EP 239 400 (Winter et al.) describes altering antibodies by substitution (within a given variable region) of their complementarity determining regions (CDRs) for one species with those from another. CDR-substituted antibodies can be less likely to elicit an immune response in humans compared to true chimeric antibodies because the CDR-substituted antibodies contain considerably less non-human components. (Riechmann et al., 1988, Nature 332, 323-327; Verhoeyen et al., 1988, Science 239, 1534-1536). Typically, CDRs of a murine antibody substituted into the corresponding regions in a human antibody by using recombinant nucleic acid technology to produce sequences encoding the desired substituted antibody. Human constant region gene segments of the desired isotype (usually gamma I for CH and kappa for CL) can be added and the heavy and light chain genes can be co-expressed in mammalian cells to produce soluble antibody. Large nonimmunized phage display libraries may also be used to isolate high affinity antibodies that can be developed as human therapeutics using standard phage technology (see, e.g., Hoogenboom et al. (1998) Immunotechnology 4:1-20; and Hoogenboom et at (2000) Immunol Today 2:371-8; U.S. 2003-0232333).

An anti-$\alpha 4$ antibody or antibody fragment described herein can recognize epitopes of the $\alpha 4$ subunit that are involved in binding to a cognate ligand, e.g., VCAM-1 or fibronectin. The antibodies described herein can inhibit binding of to one or more of the cognate ligands (e.g., VCAM-1 and fibronectin).

In some embodiments, the antibodies featured herein, can interact with VLA-4 on cells, e.g., lymphocytes, but do not cause cell aggregation.

An exemplary $\alpha 4$ binding antibody has one or more CDRs, e.g., all three heavy chain (HC) CDRs and/or all three light chain (LC) CDRs of a particular antibody disclosed herein, or CDRs that are, in sum, at least 80, 85, 90, 92, 94, 95, 96, 97, 98, 99% identical to such an antibody. In one embodiment, the H1 and H2 hypervariable loops have the same canonical structure as those of an antibody described herein. In one embodiment, the L1 and L2 hypervariable loops have the same canonical structure as those of an antibody described herein.

In one embodiment, the amino acid sequence of the HC and/or LC variable domain sequence is at least 70, 80, 85, 90, 92, 95, 97, 98, 99, or 100% identical to the amino acid sequence of the HC and/or LC variable domain of an antibody described herein. The amino acid sequence of the HC and/or LC variable domain sequence can differ by at least one amino acid, but no more than ten, eight, six, five, four, three, or two amino acids from the corresponding sequence of an antibody described herein. For example, the differences may be primarily or entirely in the framework regions.

The amino acid sequences of the HC and LC variable domain sequences can be encoded by a nucleic acid sequence that hybridizes under high stringency conditions to a nucleic acid sequence described herein or one that encodes a variable domain or an amino acid sequence described herein. In one embodiment, the amino acid sequences of one or more framework regions (e.g., FR1, FR2, FR3, and/or FR4) of the HC and/or LC variable domain are at least 70, 80, 85, 90, 92, 95, 97, 98, 99, or 100% identical to corresponding framework regions of the HC and LC variable domains of an antibody described herein. In one embodiment, one or more heavy or light chain framework regions (e.g., HC FR1, FR2, and FR3) are at least 70, 80, 85, 90, 95, 96, 97, 98, or 100% identical to the sequence of corresponding framework regions from a human germline antibody.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

As used herein, the term "hybridizes under high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. High stringency hybridization conditions include hybridization in 6×SSC at about 45° C., followed by one or more washes in 0.2×SSC, 0.1% SDS at 65° C., or substantially similar conditions.

Antibody Production

Antibodies can be produced in prokaryotic and eukaryotic cells. In one embodiment, the antibodies (e.g., scFvs) are expressed in a yeast cell such as *Pichia* (see, e.g., Powers et al. (2001) J. Immunol. Methods 251:123-35), Hanseula, or *Saccharomyces.*

In one embodiment, antibodies, particularly full length antibodies, e.g., IgGs, are produced in mammalian cells. Exemplary mammalian host cells for recombinant expression include Chinese Hamster Ovary (CHO cells) (including dhfr-CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601-621), lymphocytic cell lines, e.g., NS0 myeloma cells and SP2 cells, COS cells, K562, and a cell from a transgenic animal, e.g., a transgenic mammal. For example, the cell is a mammary epithelial cell.

In addition to the nucleic acid sequence encoding the immunoglobulin domain, the recombinant expression vectors may carry additional nucleic acid sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). Exemplary selectable marker genes include the dihydrofolate reductase (DHFR) gene (for use in dhfr$^-$ host cells with methotrexate selection/amplification) and the neo gene (for G418 selection).

In an exemplary system for recombinant expression of an antibody (e.g., a full length antibody or an antigen-binding portion thereof), a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, to transfect the host cells, to select for transformants, to culture the host cells, and to recover the antibody from the culture medium. For example, some antibodies can be isolated by affinity chromatography with a Protein A or Protein G. For example, purified α4-binding antibodies can be concentrated to about 100 mg/mL to about 200 mg/mL using protein concentration techniques that are known in the art.

Antibodies may also include modifications, e.g., modifications that alter Fc function, e.g., to decrease or remove interaction with an Fc receptor or with C1q, or both. For example, the human IgG4 constant region can have a Ser to Pro mutation at residue 228 to fix the hinge region. The amino acid sequence of an IgG4 Fc (hinge+CH2+CH3 domain) is provided in FIG. 5.

In another example, the human IgG1 constant region can be mutated at one or more residues, e.g., one or more of residues 234 and 237, e.g., according to the numbering in U.S. Pat. No. 5,648,260. Other exemplary modifications include those described in U.S. Pat. No. 5,648,260.

For some antibodies that include an Fc domain, the antibody production system may be designed to synthesize antibodies in which the Fc region is glycosylated. In another example, the Fc domain of IgG molecules is glycosylated at asparagine 297 in the CH2 domain (see FIG. 5). This asparagine is the site for modification with biantennary-type oligosaccharides. This glycosylation participates in effector functions mediated by Fey receptors and complement C1q (Burton and Woof (1992) Adv. Immunol. 51:1-84; Jefferis et al. (1998) Immunol. Rev. 163:59-76). The Fc domain can be produced in a mammalian expression system that appropriately glycosylates the residue corresponding to asparagine 297. The Fc domain can also include other eukaryotic post-translational modifications.

Other suitable Fc domain modifications include those described in WO2004/029207. For example, the Fc domain can be an XmAb® Fc (Xencor, Monrovia, CA). The Fc domain, or a fragment thereof, can have a substitution in an Fcγ Receptor (FcγR) binding region, such as the domains and fragments described in WO05/063815. In some embodiments, the Fc domain, or a fragment thereof, has a substitution in a neonatal Fc Receptor (FcRn) binding region, such as the domains and fragments described in WO05047327. In other embodiments, the Fc domain is a single chain, or fragment thereof, or modified version thereof, such as those described in WO2008143954. Other suitable Fc modifications are known and described in the art.

Antibodies can also be produced by a transgenic animal. For example, U.S. Pat. No. 5,849,992 describes a method for expressing an antibody in the mammary gland of a transgenic mammal. A transgene is constructed that includes a milk-specific promoter and nucleic acid sequences encoding the antibody of interest, e.g., an antibody described herein, and a signal sequence for secretion. The milk produced by females of such transgenic mammals includes, secreted therein, the antibody of interest, e.g., an antibody described herein. The antibody can be purified from the milk, or for some applications, used directly.

Antibodies can be modified, e.g., with a moiety that improves its stabilization and/or retention in circulation, e.g., in blood, serum, lymph, bronchoalveolar lavage, or other tissues, e.g., by at least 1.5, 2, 5, 10, or 50 fold.

For example, a VLA-4 binding antibody can be associated with a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 daltons (or about 1,000 to about 15,000, and 2,000 to about 12,500) can be used.

For example, a VLA-4 binding antibody can be conjugated to a water soluble polymer, e.g., a hydrophilic polyvinyl polymer, e.g. polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides that comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon.

Exemplary Second Agents

In some cases, the formulations described herein, e.g., formulations containing an alpha-4 binding antibody, include a second agent, or are administered in combination with a formulation containing a second agent.

In one implementation, the $\alpha 4$ binding antibody and second agent is provided as a co-formulation, and the co-formulation is administered to the subject. It is further possible, e.g., at least 24 hours before or after administering the co-formulation, to administer separately one dose of the $\alpha 4$ binding antibody formulation and then one dose of a formulation containing the second agent. In another implementation, the antibody and the second agent are provided as separate formulations, and the step of administering includes sequentially administering the antibody and the second agent. The sequential administrations can be provided on the same day (e.g., within one hour of one another or at least 3, 6, or 12 hours apart) or on different days.

Generally, the antibody and the second agent are each administered as a plurality of doses separated in time. The antibody and the second agent are generally each administered according to a regimen. The regimen for one or both may have a regular periodicity. The regimen for the antibody can have a different periodicity from the regimen for the second agent, e.g., one can be administered more frequently than the other. In one implementation, one of the antibody and the second agent is administered once weekly and the other once monthly. In another implementation, one of the antibody and the second agent is administered continuously, e.g., over a period of more than 30 minutes but less than 1, 2, 4, or 12 hours, and the other is administered as a bolus. The antibody and the second agent can be administered by any appropriate method, e.g., subcutaneously, intramuscularly, or intravenously.

In some embodiments, each of the antibody and the second agent is administered at the same dose as each is prescribed for monotherapy. In other embodiments, the antibody is administered at a dosage that is equal to or less than an amount required for efficacy if administered alone. Likewise, the second agent can be administered at a dosage that is equal to or less than an amount required for efficacy if administered alone.

Non-limiting examples of second agents for treating multiple sclerosis in combination with an $\alpha 4$ binding antibody include:

- interferons, e.g., human interferon beta-la (e.g., AVONEX® or Rebif®)) and interferon beta-1b (BETASERON™; human interferon beta substituted at position 17; Berlex/Chiron);
- glatiramer acetate (also termed Copolymer 1, Cop-1; COPAXONE™; Teva Pharmaceutical Industries, Inc.);
- Rituxan® (rituximab) or another anti-CD20 antibody, e.g., one that competes with or binds an overlapping epitope with rituximab;
- mixtoxantrone (NOVANTRONE®, Lederle);
- a chemotherapeutic, e.g., clabribine (LEUSTATIN®), azathioprine (IMURAN®), cyclophosphamide (CYTOXAN®), cyclosporine-A, methotrexate, 4-aminopyridine, and tizanidine;
- a corticosteroid, e.g., methylprednisolone (MEDRONE®, Pfizer), prednisone;
- an immunoglobulin, e.g., Rituxan® (rituximab); CTLA4 Ig; alemtuzumab (MabCAMPATH®) or daclizumab (an antibody that binds CD25);
- statins; and TNF antagonists.

Glatiramer acetate is a protein formed from a random chain of amino acids-glutamic acid, lysine, alanine and tyrosine (hence GLATiramer). Glatiramer acetate can be synthesized in solution from these amino acids at a ratio of approximately 5 parts alanine to 3 parts lysine, 1.5 parts glutamic acid and 1 part tyrosine using N-carboxyamino acid anhydrides.

Additional second agents include antibodies or antagonists of other human cytokines or growth factors, for example, TNF, LT, IL-1, IL-2, IL-6, IL-7, IL-8, IL-12 IL-15, IL-16, IL-18, EMAP-11, GM-CSF, FGF, and PDGF. Still other exemplary second agents include antibodies to cell surface molecules such as CD2, CD3, CD4, CD8, CD25, CD28, CD30, CD40, CD45, CD69, CD80, CD86, CD90 or their ligands. For example, daclizubmab is an anti-CD25 antibody that may ameliorate multiple sclerosis.

Still other exemplary antibodies include antibodies that provide an activity of an agent described herein, such as an antibody that engages an interferon receptor, e.g., an interferon beta receptor. Typically, in implementations in which the second agent includes an antibody, it binds to a target protein other than VLA-4 or other than α4 integrin, or at least an epitope on VLA-4 other than one recognized by the first agent.

Still other additional exemplary second agents include: FK506, rapamycin, mycophenolate mofetil, leflunomide, non-steroidal anti-inflammatory drugs (NSAIDs), for example, phosphodiesterase inhibitors, adenosine agonists, antithrombotic agents, complement inhibitors, adrenergic agents, agents that interfere with signaling by proinflammatory cytokines as described herein, IL-1β converting enzyme inhibitors (e.g., Vx740), anti-P7s, PSGL, TACE inhibitors, T-cell signaling inhibitors such as kinase inhibitors, metalloproteinase inhibitors, sulfasalazine, azathloprine, 6-mercaptopurines, angiotensin converting enzyme inhibitors, soluble cytokine receptors and derivatives thereof, as described herein, anti-inflammatory cytokines (e.g. IL-4, IL-10, IL-13 and TGF).

In some embodiments, a second agent may be used to treat one or more symptoms or side effects of MS. Such agents include, e.g., amantadine, baclofen, papaverine, meclizine, hydroxyzine, sulfamethoxazole, ciprofloxacin, docusate, pemoline, dantrolene, desmopressin, dexamethasone, tolterodine, phenytoin, oxybutynin, bisacodyl, venlafaxine, amitriptyline, methenamine, clonazepam, isoniazid, vardenafil, nitrofurantoin, *psyllium* hydrophilic mucilloid, alprostadil, gabapentin, nortriptyline, paroxetine, propantheline bromide, modafinil, fluoxetine, phenazopyridine, methylprednisolone, carbamazepine, imipramine, diazepam, sildenafil, bupropion, and sertraline. Many second agents that are small molecules have a molecular weight between 150 and 5000 Daltons.

Examples of TNF antagonists include chimeric, humanized, human or in vitro generated antibodies (or antigen-binding fragments thereof) to TNF (e.g., human TNF a), such as D2E7, (human TNFα antibody, U.S. Pat. No. 6,258,562; BASF), CDP-571/CDP-870/BAY-10-3356 (humanized anti-TNFα antibody; Celltech/Pharmacia), cA2 (chimeric anti-TNFα antibody; REMICADE™, Centocor); anti-TNF antibody fragments (e.g., CPD870); soluble fragments of the TNF receptors, e.g., p55 or p75 human TNF receptors or derivatives thereof, e.g., 75 kdTNFR-IgG (75 kD TNF receptor-IgG fusion protein, ENBREL™; Immunex; see e.g., Arthritis & Rheumatism (1994) Vol. 37, 5295; J. Invest. Med. (1996) Vol. 44, 235A), p55 kdTNFR-IgG (55 kD TNF receptor-IgG fusion protein (LENERCEPT™)); enzyme antagonists, e.g., TNFα converting enzyme (TACE) inhibitors (e.g., an alpha-sulfonyl hydroxamic acid derivative, WO 01/55112, and N-hydroxyformamide TACE inhibitor GW 3333, –005, or –022); and TNF-bp/s-TNFR (soluble TNF binding protein; see e.g., Arthritis & Rheumatism (1996) Vol. 39, No. 9 (supplement), 5284; Amer. J. Physiol.-Heart and Circulatory Physiology (1995) Vol. 268, pp. 37-42).

In addition to a second agent, it is also possible to deliver other agents to the subject. However, in some embodiments, no protein or no biologic, other than the α4 binding antibody and second agent, are administered to the subject as a pharmaceutical composition. The α4 binding antibody and the second agent may be the only agents that are delivered by injection. In embodiments in which the second agent is a recombinant protein, the α4 binding antibody and second agent may be the only recombinant agents administered to the subject, or at least the only recombinant agents that modulate immune or inflammatory responses. In still other embodiments, the α4 binding antibody alone is the only recombinant agent or the only biologic administered to the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLE

Example 1. Variant Anti-VLA-4 Antibodies are More Potent than Humanized HP1/2

Anti-VLA-4 antibodies were constructed using the germline framework IGKV4-1 (or design L1 and L2) or germline-engineered AAH7033.1 (for design L3) for the VL chain and germline framework IGHV1-f for VH. These antibodies had fewer back mutations than the humanized HP1/2 antibody described in U.S. Pat. No. 6,602,503.

Heavy Chain Variations

The sequences of three variations of the heavy chain are shown in FIG. 1 as Design H0, Design H1 and Design H2. Each design has the CDR's of murine HP1/2 grafted into the IGHV1-f framework. Design H0 includes no back mutations of the framework regions, while Designs H1 and H2 have various degrees of back mutations in the framework regions sequences to optimize the affinity of the humanized antibody.

Light Chain Variations

Figure 2:
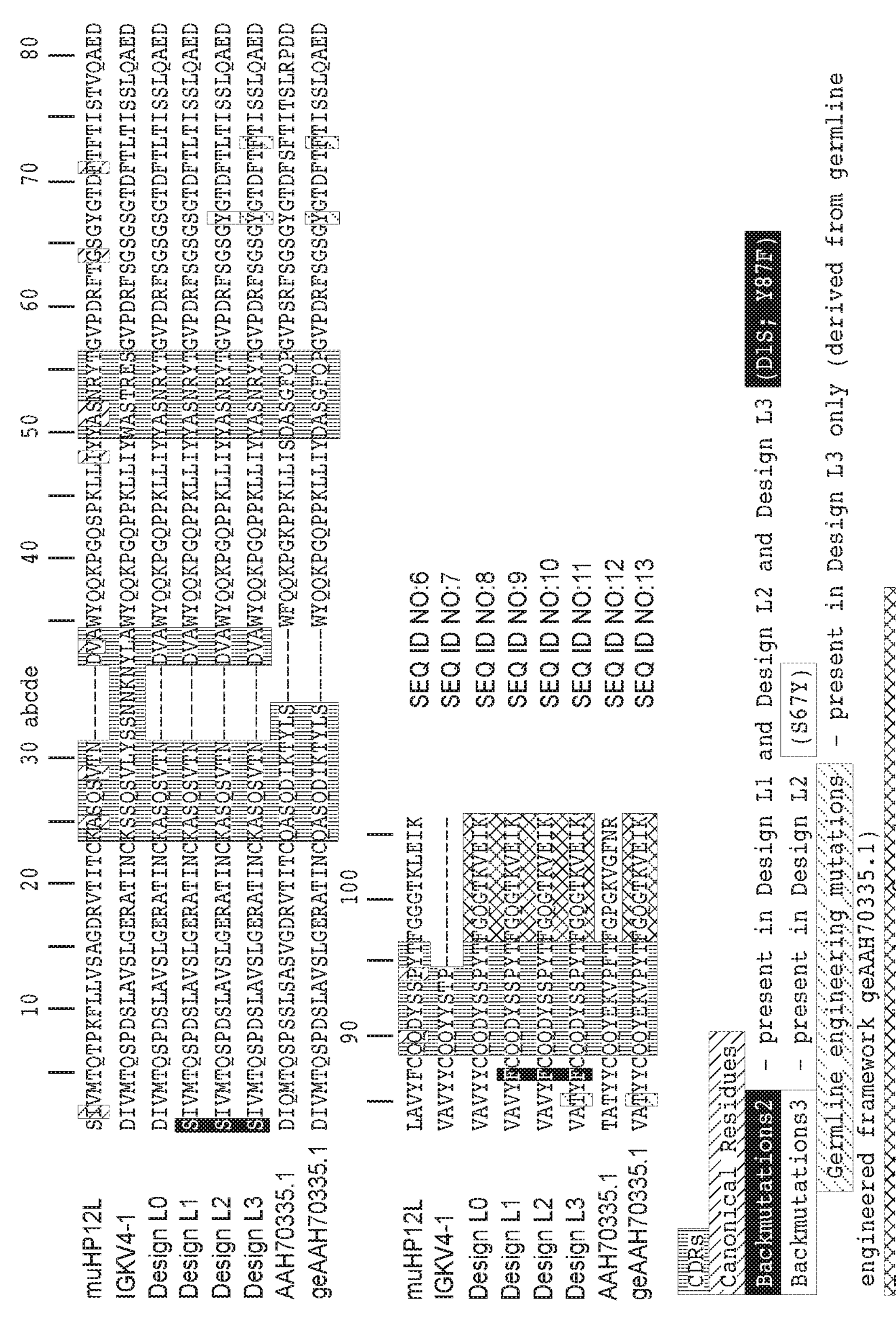
FIG. 2 displays the four sequence variants of HP1/2 light chain to a germline IGKV4-1 antibody sequence (Design L0, L1, and L2) or human kappa germline engineered AAH7033.1 antibody sequence (Design L3). The lower case letters above the sequence represent insertions according to the Kabat numbering scheme.

The sequences of four variations of the light chain are shown in FIG. 2 as Design L0, Design L1, Design L2 and Design L3 (also called L0, L1, L2, L3). Each design has the CDR's of murine HP1/2 grafted into the germline framework. The IGKV4-1 germline framework was used for Designs L0, L1, and L2, and the AAH70335 germline engineered framework was used for Design L3. Design L0 includes no back mutations of the framework regions, while Designs L1, L2, and L3 have various degrees of back mutations in the framework regions to optimize the affinity of the humanized antibody.

Figure 3:
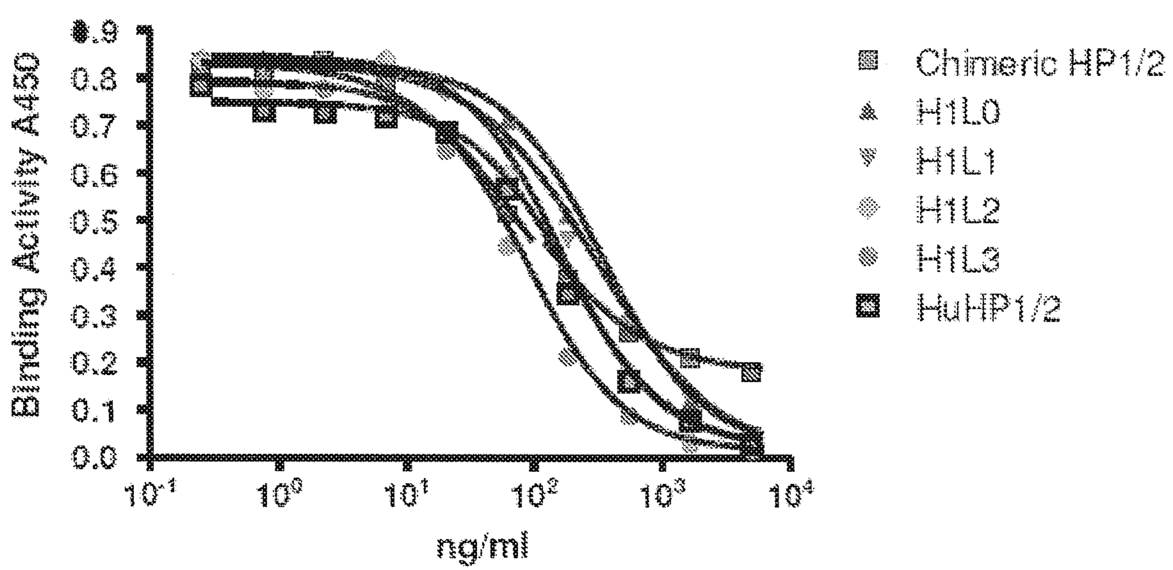
FIG. 3 is a graph depicting the results of ELISA assays.

The results of competition ELISA assays are shown in Table 1 and FIG. 3. In this experiment α4β1 was preincubated with testing mAb and then murine HP1/2 was used as competing reagent. The results of this experiment indicated that the antibodies having light chains L2 or L3 were more potent than the humanized antibody HuHP1/2 described in U.S. Pat. No. 6,602,503. The results are shown in Table 1 below, and in FIG. 3. The heavy chain (H1) in the antibodies for this assay had the "Design H1" sequence shown in FIG. 1, whereas L1 refers to Design L1 in FIG. 2.

TABLE 1

Competition Assay by ELISA

| mAb | IC50 nM |
|---|---|
| Chimeric HP1/2 | 1.06 |
| H1L0 | 1.87 |

TABLE 1-continued

| Competition Assay by ELISA | |
|---|---|
| mAb | IC50 nM |
| H1L1 | 1.67 |
| H1L2 | 0.9 |
| H1L3 | 0.49 |
| HuHP1/2 | 1.05 |

In Table 1, the chimeric mAb is chimerized HP1/2 antibody, where murine variable heavy and light chains are genetically fused to human IgG1 constant regions. This antibody is essentially identical in binding affinity to the original murine HP1/2 antibody (Sanchez-Madrid et al., Eur. J. Immunol. 16:1343-1349, 1996). The results of the experiment indicate that it is possible to improve the affinity of the monoclonal antibody relative to its murine parental sequence through humanization on germline-engineered acceptor framework.

Figure 4:
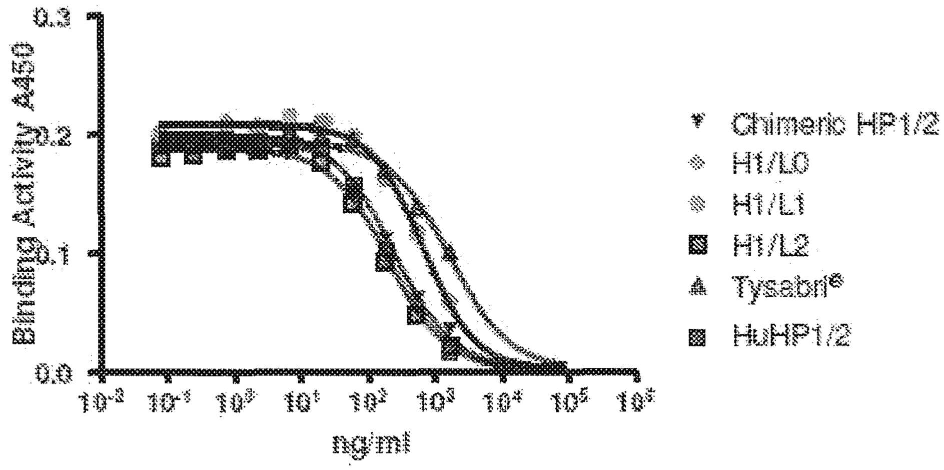
FIG. 4 is a graph depicting the results of ELISA assays.

Another competition assay compares the binding affinity of the new antibodies with the humanized 21.6 anti-α4 antibody (Tysabri® (natalizumab)) described in U.S. Pat. No. 5,840,299. In this experiment the binding of mixture of mouse HP1/2 with testing mAb to α4β1 was assayed. The results of this experiment are shown in FIG. 4 and in Table 2 below, and indicate that the newly designed antibodies are about 10-fold more potent than natalizumab.

TABLE 2

| Competition Assay by ELISA | |
|---|---|
| mAb | IC50 nM |
| Chimeric HP1/2 | 1.64 |
| H1L0 | 4.46 |
| H1L1 | 4.55 |
| H1L2 | 1.34 |
| HuHP1/2 | 1.41 |
| Tysabri ® | 10.9 |

Example 2. Humanized HP1/2 (HuHP1/2) Binds VLA-4 on Tumor Cell Lines

Figure 6:
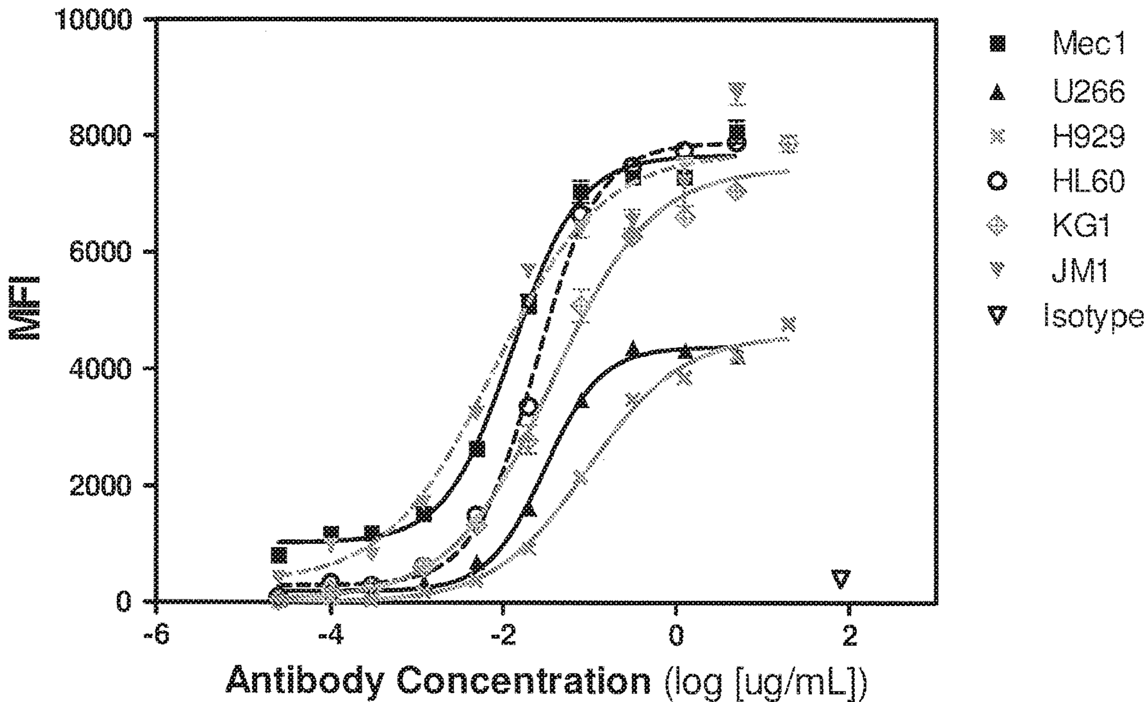
FIG. 6 is a graph depicting flow cytometry data from binding of HuHP1/2 to various tumor cell lines. "HP1/2" refers to humanized HP1/2.

Binding of anti-VLA-4 antibody HuHP1/2 to a variety of cell lines was tested by flow cytometry. Binding was tested on CLL (chronic lymphocytic leukemic) cell lines Mec1 and JM1; on MM (multiple myeloma) cell lines U266 and H929; and on AML (acute myelogenous leukemic) cell lines HL60 and KG1. HuHP1/2 bound all tumor cell lines tested (FIG. 6). The flow cytometry data was used to calculate the EC50 values for antibody binding to each of the different cell lines. This information is shown below in Table 3.

Figure 7A:
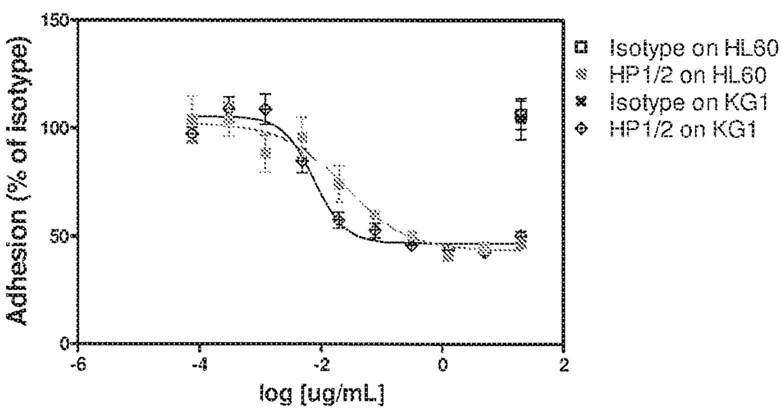
FIGS. 7A-7C is a panel of graphs depicting inhibition of binding of AML cell lines to fibronectin or VCAM1-Ig coated wells by HuHP1/2.
Figure 7B:
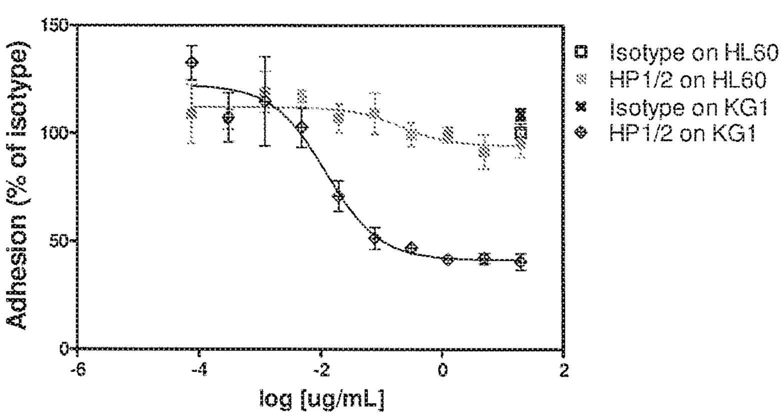
Figure 7C:
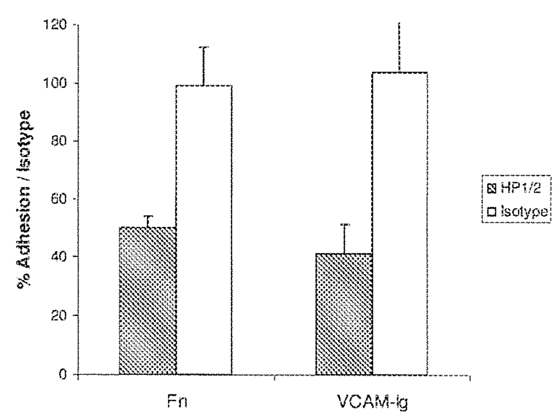

HuHP1/2 was also found to block adhesion of AML cell lines to fibronectin (FN) and VCAM1-Ig fusion protein. To test whether the antibody could block adhesion, AML cell lines HL60 or KG1 were allowed to adhere to FN-coated wells (FIG. 7A) or VCAM1-Ig-coated wells (FIG. 7B) in the presence of increasing concentrations of HP1/2 or isotype control antibody. HuHP1/2 blocked adhesion of both cell types to FN-coated wells and VCAM1-Ig-coated wells. The maximal inhibition of HL60 cell binding to both ligands was achieved with 20 μg/ml HuHP1/2 (FIG. 7C).

Figure 8A:
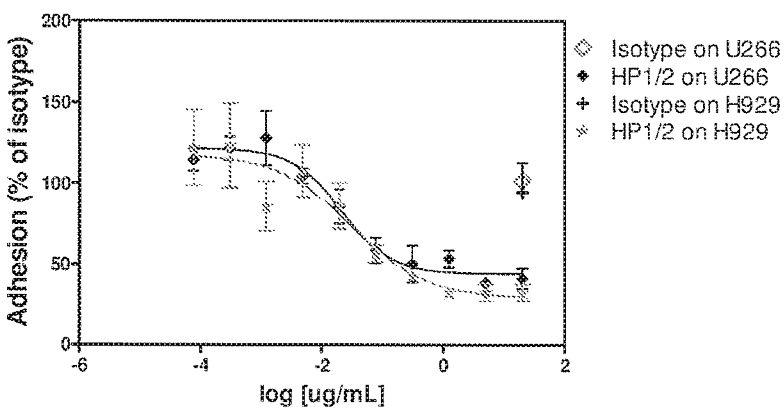
FIGS. 8A-8C make up a panel of graphs depicting inhibition of binding of MM cell lines to fibronectin or VCAM1-Ig coated wells by HuHP1/2.
Figure 8B:
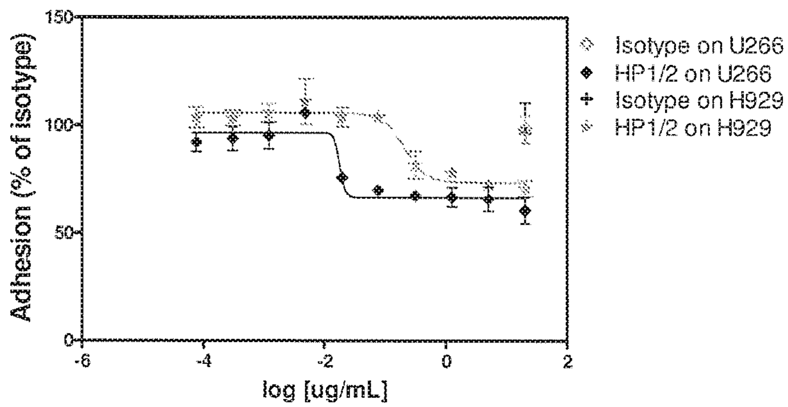
Figure 8C:
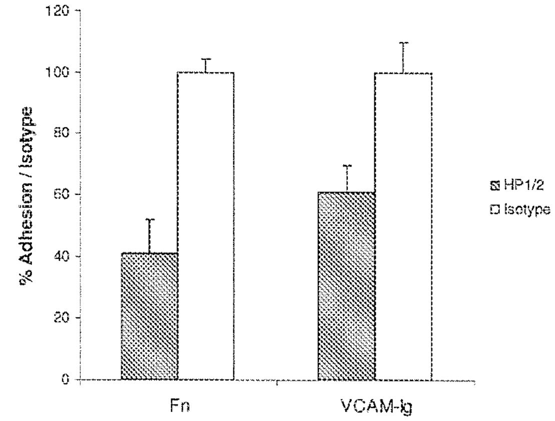

HuHP1/2 was also found to block adhesion of MM cell lines to FN and VCAM1-Ig fusion protein. The MM cell lines U266 and H929 were allowed to adhere to FN-coated wells (FIG. 8A) or VCAM1-Ig-coated wells (FIG. 8B) in the presence of increasing concentrations of HP1/2 or isotype control antibody. HuHP1/2 blocked adhesion of both types of cell lines to FN- and VCAM1-Ig-coated wells. The maximal inhibition of U266 cell binding to both ligands was achieved with 20 μg/mL HuHP1/2 (FIG. 8C).

HuHP1/2 was also found to block adhesion of CLL cell lines to FN and VCAM1-Ig fusion protein. The CLL cell lines Mec1 and JM1 were allowed to adhere to FN-coated wells (FIG. 9A) or VCAM1-Ig-coated wells (FIG. 9B) in the presence of increasing concentrations of HP1/2 or isotype control antibody. HuHP1/2 blocked adhesion of both types of cell lines to FN- and VCAM1-Ig-coated wells. The maximal inhibition of Mec1 cell binding to both ligands was achieved with 20 μg/ml HuHP1/2 (FIG. 9C).

The IC50 values for HuHP1/2 binding to the tumor cell lines were calculated from the data shown in FIGS. 7-9. These data are shown in Table 3.

TABLE 3

| Quantitation of HuHP1/2 on tumor cell lines | | | | |
|---|---|---|---|---|
| | | | $IC_{50}$ (nM) | |
| | | $EC_{50}$ (nM) | Fibronectin | VCAM |
| CLL | Mec1 | 0.11 | 0.10 | 0.07 |
| | JM1 | 0.21 | — | 0.12 |
| MM | U266 | 0.46 | 0.14 | 0.13 |
| | H929 | 0.91 | 0.21 | 1.35 |
| AML | HL60 | 0.11 | 0.16 | 0.91 |
| | KG1 | 0.19 | 0.05 | 0.1 |

Other embodiments are in the claims.

The invention claimed is:

1. A method of inhibiting binding of VLA-4 to VCAM-1 and/or fibronectin in a subject, comprising administering to the subject a recombinant anti-α4 antibody molecule, or α4-binding fragment thereof, comprising: (a) a variable light chain comprising the amino acid sequence of SEQ ID NO: 11; and (b) a variable heavy chain comprising the amino acid sequence of SEQ ID NO: 4.

2. The method according to claim 1, wherein the subject has cancer.

3. The method of claim 2, wherein said cancer is selected from the group consisting of a solid tumor, a hematological malignancy, a multiple myeloma and acute myelogenous leukemia (AML).

4. The method of claim 1, wherein the subject has a disorder selected from the group consisting of an inflammatory disorder, multiple sclerosis, asthma, rheumatoid arthritis, diabetes, optic neuritis, Crohn's disease, an acute disorder, a spinal cord injury and traumatic brain injury.

5. The method of claim 1, wherein the recombinant anti-α4 antibody molecule, or α4-binding fragment thereof is administered as a regimen.

6. The method of claim 1, further comprising administering to the subject a second therapeutic agent.

7. The method of claim 6, wherein the second therapeutic agent is selected from the group consisting of a thrombolytic agent, a chemotherapeutic agent, a neuroprotective agent, an anti-inflammatory agent, a steroid, a cytokine, and a growth factor.

8. The method according to claim 2, wherein said cancer is a solid tumor.

9. The method according to claim 1, wherein the subject has a hematological malignancy.

10. The method according to claim 1, wherein the subject has multiple myeloma or acute myelogenous leukemia (AML).

11. The method according to claim 1, wherein the subject has an inflammatory disorder.

12. The method according to claim 1, wherein the subject has a disease or disorder selected from the group consisting of multiple sclerosis, asthma, rheumatoid arthritis, diabetes, optic neuritis, and Crohn's disease.

13. The method according to claim 1, wherein the subject has acute CNS injury, acute myelogenous leukemia parentheses (AML), acute lymphoblastic leukemia (ALL), acute erythroleukemia, acute primary eosinophilic pneumonia, acute coronary syndrome (ACS) or acute myocardial infarction.

14. The method according to claim 1, wherein the subject has a spinal cord injury or traumatic brain injury.

* * * * *

SEQUENCE LISTING

```
Sequence total quantity: 15
SEQ ID NO: 1           moltype = AA  length = 121
FEATURE                Location/Qualifiers
source                 1..121
                       mol_type = protein
                       organism = Mus sp.
SEQUENCE: 1
EVQLQQSGAE LVKPGASVKL SCTASGFNIK DTYMHWVKQR PEQGLEWIGR IDPASGDTKY  60
DPKFQVKATI TADTSSNTAW LQLSSLTSED TAVYYCADGM WVSTGYALDF WGQGTTVTVS  120
S                                                                 121

SEQ ID NO: 2           moltype = AA  length = 98
FEATURE                Location/Qualifiers
source                 1..98
                       mol_type = protein
```

```
                         organism = Homo sapiens
SEQUENCE: 2
EVQLVQSGAE VKKPGATVKI SCKVSGYTFT DYYMHWVQQA PGKGLEWMGL VDPEDGETIY  60
AEKFQGRVTI TADTSTDTAY MELSSLRSED TAVYYCAT                          98

SEQ ID NO: 3             moltype = AA  length = 121
FEATURE                  Location/Qualifiers
REGION                   1..121
                         note = source = /note="Description of Artificial Sequence:
                          Synthetic polypeptide"
source                   1..121
                         mol_type = protein
                         organism = synthetic construct
SEQUENCE: 3
EVQLVQSGAE VKKPGATVKI SCKVSGFNIK DTYMHWVQQA PGKGLEWMGR IDPASGDTKY  60
DPKFQVRVTI TADTSTDTAY MELSSLRSED TAVYYCATGM WVSTGYALDF WGQGTLVTVS  120
S                                                                  121

SEQ ID NO: 4             moltype = AA  length = 121
FEATURE                  Location/Qualifiers
REGION                   1..121
                         note = source = /note="Description of Artificial Sequence:
                          Synthetic polypeptide"
source                   1..121
                         mol_type = protein
                         organism = synthetic construct
SEQUENCE: 4
EVQLVQSGAE VKKPGATVKI SCKASGFNIK DTYMHWVQQA PGKGLEWMGR IDPASGDTKY  60
DPKFQVRVTI TADTSTDTAY MELSSLRSED TAVYYCADGM WVSTGYALDF WGQGTLVTVS  120
S                                                                  121

SEQ ID NO: 5             moltype = AA  length = 121
FEATURE                  Location/Qualifiers
REGION                   1..121
                         note = source = /note="Description of Artificial Sequence:
                          Synthetic polypeptide"
source                   1..121
                         mol_type = protein
                         organism = synthetic construct
SEQUENCE: 5
EVQLVQSGAE VKKPGATVKI SCKASGFNIK DTYMHWVQQA PGKGLEWIGR IDPASGDTKY  60
DPKFQVRATI TADTSTNTAY LELSSLRSED TAVYYCADGM WVSTGYALDF WGQGTLVTVS  120
S                                                                  121

SEQ ID NO: 6             moltype = AA  length = 107
FEATURE                  Location/Qualifiers
source                   1..107
                         mol_type = protein
                         organism = Mus sp.
SEQUENCE: 6
SIVMTQTPKF LLVSAGDRVT ITCKASQSVT NDVAWYQQKP GQSPKLLIYY ASNRYTGVPD  60
RFTGSGYGTD FTFTISTVQA EDLAVYFCQQ DYSSPYTFGG GTKLEIK                107

SEQ ID NO: 7             moltype = AA  length = 101
FEATURE                  Location/Qualifiers
source                   1..101
                         mol_type = protein
                         organism = Homo sapiens
SEQUENCE: 7
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYST P                      101

SEQ ID NO: 8             moltype = AA  length = 107
FEATURE                  Location/Qualifiers
REGION                   1..107
                         note = source = /note="Description of Artificial Sequence:
                          Synthetic polypeptide"
source                   1..107
                         mol_type = protein
                         organism = synthetic construct
SEQUENCE: 8
DIVMTQSPDS LAVSLGERAT INCKASQSVT NDVAWYQQKP GQPPKLLIYY ASNRYTGVPD  60
RFSGSGSGTD FTLTISSLQA EDVAVYYCQQ DYSSPYTFGQ GTKVEIK                107

SEQ ID NO: 9             moltype = AA  length = 107
FEATURE                  Location/Qualifiers
REGION                   1..107
                         note = source = /note="Description of Artificial Sequence:
                          Synthetic polypeptide"
```

```
source                  1..107
                        mol_type = protein
                        organism = synthetic construct
SEQUENCE: 9
SIVMTQSPDS LAVSLGERAT INCKASQSVT NDVAWYQQKP GQPPKLLIYY ASNRYTGVPD  60
RFSGSGSGTD FTLTISSLQA EDVAVYFCQQ DYSSPYTFGQ GTKVEIK               107

SEQ ID NO: 10           moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 10
SIVMTQSPDS LAVSLGERAT INCKASQSVT NDVAWYQQKP GQPPKLLIYY ASNRYTGVPD  60
RFSGSGYGTD FTLTISSLQA EDVAVYFCQQ DYSSPYTFGQ GTKVEIK               107

SEQ ID NO: 11           moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 11
SIVMTQSPDS LAVSLGERAT INCKASQSVT NDVAWYQQKP GQPPKLLIYY ASNRYTGVPD  60
RFSGSGYGTD FTFTISSLQA EDVATYFCQQ DYSSPYTFGQ GTKVEIK               107

SEQ ID NO: 12           moltype = AA  length = 107
FEATURE                 Location/Qualifiers
source                  1..107
                        mol_type = protein
                        organism = Homo sapiens
SEQUENCE: 12
DIQMTQSPSS LSASVGDRVT ITCQASQDIK TYLSWFQQKP GKPPKLLISD ASGFQPGVPS  60
RFSGSGYGTD FSFTITSLRP DDTATYYCQQ YEKVPFTFGP GKVGFNR               107

SEQ ID NO: 13           moltype = AA  length = 107
FEATURE                 Location/Qualifiers
REGION                  1..107
                        note = source = /note="Description of Artificial Sequence:
                         Synthetic polypeptide"
source                  1..107
                        mol_type = protein
                        organism = synthetic construct
SEQUENCE: 13
DIVMTQSPDS LAVSLGERAT INCQASQDIK TYLSWYQQKP GQPPKLLIYD ASGFQPGVPD  60
RFSGSGYGTD FTFTISSLQA EDVATYYCQQ YEKVPYTFGQ GTKVEIK               107

SEQ ID NO: 14           moltype = AA  length = 228
FEATURE                 Location/Qualifiers
REGION                  1..228
                        note = source = /note="Description of Artificial Sequence:
                         Synthetic polypeptide"
source                  1..228
                        mol_type = protein
                        organism = synthetic construct
SEQUENCE: 14
ESKYGPPCPS CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLG              228

SEQ ID NO: 15           moltype = AA  length = 236
FEATURE                 Location/Qualifiers
source                  1..236
                        mol_type = protein
                        organism = Homo sapiens
SEQUENCE: 15
MDMRVPAQLL GLLLLWLSGA RCDIQMTQSP SSLSASVGDR VTITCQASQD IKTYLSWFQQ  60
KPGKPPKLLI SDASGFQPGV PSRFSGSGYG TDFSFTITSL RPDDTATYYC QQYEKVPFTF  120
GPGTKVGFNR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236
```